US012655390B2

(12) United States Patent
Hosoi et al.

(10) Patent No.: US 12,655,390 B2
(45) Date of Patent: Jun. 16, 2026

(54) CHIMERIC ANTIGEN RECEPTOR GENE-MODIFIED LYMPHOCYTE HAVING CYTOCIDAL EFFECT

(71) Applicants: Shinshu University, Matsumoto City (JP); Kyoto Prefectural Public University Corporation, Kyoto (JP)

(72) Inventors: Hajime Hosoi, Kyoto (JP); Tomoko Iehara, Kyoto (JP); Shigeki Yagyu, Kyoto (JP); Yozo Nakazawa, Matsumoto City (JP)

(73) Assignees: Shinshu University, Matsumoto City (JP); Kyoto Prefectural Public University Corporation, Kyoto (JP)

( * ) Notice: Subject to any disclaimer, the term of this patent is extended or adjusted under 35 U.S.C. 154(b) by 637 days.

(21) Appl. No.: 18/168,135

(22) Filed: Feb. 13, 2023

(65) Prior Publication Data

US 2023/0295568 A1     Sep. 21, 2023

Related U.S. Application Data

(63) Continuation-in-part of application No. 16/469,553, filed as application No. PCT/JP2017/043729 on Dec. 6, 2017, now abandoned.

(30) Foreign Application Priority Data

Dec. 14, 2016     (JP) ................................. 2016-242054

(51) Int. Cl.
| | | |
|---|---|---|
| *C12N 5/0783* | (2010.01) | |
| *A61P 35/00* | (2006.01) | |
| *C07K 14/705* | (2006.01) | |

(52) U.S. Cl.
CPC ............ *C12N 5/0636* (2013.01); *A61P 35/00* (2018.01); *C07K 14/7051* (2013.01); *C07K 14/70521* (2013.01); *C07K 2319/02* (2013.01); *C07K 2319/03* (2013.01); *C12N 2510/00* (2013.01)

(58) Field of Classification Search
CPC ... C12N 5/0636; C12N 2510/00; A61P 35/00; C07K 2319/02; C07K 2319/03; A61K 40/11; A61K 40/31; A61K 40/422
See application file for complete search history.

(56) References Cited

U.S. PATENT DOCUMENTS

| | | | |
|---|---|---|---|
| 8,906,682 | B2 | 12/2014 | June et al. |
| 2005/0084873 | A1 | 4/2005 | Krasnoperov et al. |
| 2005/0249736 | A1* | 11/2005 | Krasnoperov ......... C07K 16/30 |
| | | | 536/23.53 |
| 2010/0022569 | A1 | 1/2010 | Manley et al. |
| 2010/0154070 | A1 | 6/2010 | Xu et al. |

| | | | |
|---|---|---|---|
| 2013/0165475 | A1 | 6/2013 | Jiang et al. |
| 2016/0053017 | A1 | 2/2016 | Orentas et al. |
| 2022/0025369 | A1 | 1/2022 | Fotin-Mleczek et al. |

FOREIGN PATENT DOCUMENTS

| | | | |
|---|---|---|---|
| JP | 2008-545375 A | 12/2008 | |
| JP | 2011-256179 A | 12/2011 | |
| JP | 2013-189443 A | 9/2013 | |
| JP | 2013-536806 A | 9/2013 | |
| SG | 190997 A1 * | 7/2013 | ..... A61K 39/001112 |
| WO | 02/26827 A1 | 4/2002 | |
| WO | 2004/080418 A2 | 9/2004 | |
| WO | 2006/122442 A1 | 11/2006 | |
| WO | 2007/137981 A1 | 12/2007 | |
| WO | 2012/028106 A1 | 3/2012 | |

OTHER PUBLICATIONS

Sadelain et. al. "The Basic Principles of Chimeric Antigen Receptor Design", Cancer Discovery, 2013, 3(4), 388-398. (Year: 2013).*
Hedge et. al. "Tandem CAR T cells targeting HER2 and IL13Rα2 mitigate tumor antigen escape", J. Clin. Invest., 2016, 126(8), 3036-3052. (Year: 2016).*
Dimasi et. al. "Development of a Trispecific Antibody Designed to Simultaneously and Efficiently Target Three Different Antigens on Tumor Cells", Mol. Pharmaceutics, 2015, 12, 3490-3501. (Year: 2015).*
Wall et al. "Transgenic livestock: progress and prospects for the future", Theriogenology, 1996, vol. 45, p. 57-68. (Year: 1996).*
Houdebine, LM, "Production of pharmaceutical proteins from transgenic animals", Journal of Biotechnology, 1994, vol. 34, p. 269-287. (Year: 1994).*
Kappel et al. "Regulating gene expression in transgenic animals", Current Opinions in Biotechnology, 1992, vol. 3, p. 548-553. (Year: 1992).*
Houdebine, LM, "Production of pharmaceutical proteins by transgenic animals", Comparative Immunology, Microbiology, and Infectious Diseases, 2009 vol. 32, p. 107-121. (Year: 2009).*
Stammes, et. al. "Evaluation of EphA2 and EphB4 as Targets for Image-Guided Colorectal Cancer Surgery", 2017, Int. J. Mol. Sci., 18(307), 1-10. (Year: 2017).*
Z. Eshhar et al., "Specific activation and targeting of cytotoxic lymphocytes through chimeric single chains consisting of antibody-binding domains and the gamma or zeta subunits of the immunoglobulin and T-cell receptors," Proc Natl Acad Sci U S A. vol. 90, Jan. 1993, pp. 720-724. (discussed in the spec).

(Continued)

*Primary Examiner* — Laura B Goddard
*Assistant Examiner* — Alyssa Rae Stonebraker
(74) *Attorney, Agent, or Firm* — Troutman Pepper Locke LLP

(57)     ABSTRACT

An object of the present invention is to provide a therapeutic strategy in the solid tumor area and a method and a composition useful therefor to further advance the clinical application of CAR therapy. There is prepared a gene-modified lymphocyte which expresses a chimeric antigen receptor having an EphrinB2 extracellular domain at the antigen recognition site.

3 Claims, 11 Drawing Sheets
Specification includes a Sequence Listing.

(56) References Cited

OTHER PUBLICATIONS

R. Brentjens et al. "CDI9-targeted T cells rapidly induce molecular remissions in adults with chemotherapy-refractory acute lymphoblastic leukemia," Sci Transl Med. 2013; 5(177): 177ra38, pp. 1-19. (discussed in the spec).

C. U. Louis et al., "Antitumor activity and long-term fate of chimeric antigen receptor-positive T cells in patients with neuroblastoma," Blood, Dec. 1, 2011, vol. 118, No. 23, pp. 6050-6056 and information sheet. (discussed in the spec).

N. Ahmed et al., "Human Epidermal Growth Factor Receptor 2 (HER2)—Specific Chimeric Antigen Receptor-Modified T Cells for the Immunotherapy of HER2-Positive Sarcoma," J Clin Oncol., May 20, 2015, vol. 33, No. 15, pp. 1688-1696 and information sheets. (discussed in the spec).

D. Abate-Daga et al., "CAR models: next-generation CAR modifications for enhanced T-cell function," Mol Therapy—Oncolytics 2016, 3; 16014, pp. 1-7. (discussed in the spec).

S. S. Gerety et al., "Symmetrical Mutant Phenotypes of the Receptor EphB4 and Its Specific Transmembrane Ligand ephrin-B2 in Cardiovascular Development," Mol. Cell. vol. 4, Sep. 1999, pp. 403-414. (discussed in the spec).

J. Lv et al., "EphB4 promotes the proliferation, invasion, and angiogenesis of human colorectal cancer," Exp Mol Pathol. 100, 2016, pp. 402-408. (cited in the ISR) (discussed in the spec).

S. Pradeep et al., "Erythropoietin Stimulates Tumor Growth via EphB4," Cancer Cell 28, Nov. 9, 2015, pp. 610-622. (discussed in the spec).

B. D. Ferguson et al., "Novel EPHB4 Receptor Tyrosine Kinase Mutations and Kinomic Pathway Analysis in Lung Cancer," Scientific Report 5, Jun. 15, 2015, 10641, pp. 1-15. (discussed in the spec).

M. Becerikli M et al., "EPHB4 tyrosine-kinase receptor expression and biological significance in soft tissue sarcoma," Int'l Journal of Cancer, 136, 2015, pp. 1781-1791. (discussed in the spec).

I. Mertens-Walker et al., "EphB4 localises to the nucleus of prostate cancer cells," Exp Cell Res. 333, 2015, pp. 105-115. (discussed in the spec).

B. D. Ferguson et al., "Expression of the EPHB4 receptor tyrosine kinase in head and neck and renal malignancies—implications for solid tumors and potential for therapeutic inhibition," Growth Factors, 43(6), Dec. 2014, pp. 202-206 and information sheets. (discussed in the spec).

M. I. Aslam et al., "PDGFRbeta reverses EphB4 signaling in alveolar rhabdomyosarcoma," PNAS, vol. 111, No. 17, Apr. 29, 2014, pp. 6383-6388. (discussed in the spec).

Schmitt F et al., "Eph receptor B4 is a regulator of estrogen receptor alpha in breast cancer cells," J Recept Signal Transduct Res. 33(4), 2013, Abstract. (discussed in the spec).

B. D. Ferguson et al., "The EphB4 Receptor Tyrosine Kinase Promotes Lung Cancer Growth: A Potential Novel Therapeutic Target," PLOS, vol. 8, Issue 7, Jul. 2013 e67668, pp. 1-16. (discussed in the spec).

R. Liu et al., "EphB4 as a therapeutic target in mesothelioma," BMC Cancer, 2013, 13:269, pp. 1-7. (discussed in the spec).

M. Li et al., "Clinical implications of EphB4 receptor expression in pancreatic cancer," Mol Biol Rep, vol. 40, 2013, pp. 1735-1741. (discussed in the spec).

R. Hasina et al., "Critical Role for the Receptor Tyrosine Kinase EPHB4 in Esophageal Cancers," Cancer Res; 73(1), Jan. 1, 2013, pp. 184-194 and information sheet. (discussed in the spec).

R. Rutkowski et al., "Evidence for a dual function of EphB4 as tumor promoter and suppressor regulated by the absence or presence of the ephrin-B2 ligand," Int'l Journal of Cancer, 131, 2012, pp. E614-E624. (discussed in the spec).

N. K. Noren et al., "The EphB4 receptor suppresses breast cancer cell tumorigenicity through an Abl-Crk pathway," Nature Cell Biology, vol. 8, No. 8, Aug. 2006, pp. 815-825. (cited in the ISR) (discussed in the spec).

J. Aitsebaomo et al., "Brothers and Sisters: Molecular Insights Into Arteria-Venous Heterogeneity," Circ Res. 2008; 103; 929-939. (discussed in the spec).

Boyd AW et al., "Therapeutic targeting of EPH receptors and their ligands," Nat Rev Drug Discovery, Jan. 2014, 13(1), Abstract. (discussed in the spec).

T. Nakagawa et al., "Development of next-generation adoptive immunotherapy using cytotoxic T-lymphocyte (CTL) expressing chimeric antigen-receptor (CAR)," Drug Delivery System 2013; 28-1, pp. 35-44. (cited in the ISR).

Y. Nakazawa, "Gene-modified T-cell Therapy Using Chimeric Antigen Receptor," Shinsyu Medical Journal, 61(4), 2013, pp. 197-203. (cited in the ISR).

S. Saito et al., "Anti-leukemic potency of piggyBac-mediated CD19-specific T cells against refractory Philadelphia chromosome—positive acute lymphoblastic leukemia," Cytotherapy 2014; 16, pp. 1257-1269. (cited in the ISR).

International Search Report mailed Feb. 20, 2018, issued for PCT/JP2017/043729.

Michael H. Kershaw et al., "Gene-engineered T cells for cancer therapy", Nature Reviews Cancer, vol. 13, No. 8, Aug. 1, 2013, pp. 525-541. (cited in the Jun. 17, 2020 Search Report issued for EP17881391.1).

Supplementary European Search Report dated Jun. 17, 2020, issued for European Patent Application No. 17881391.1.

Moingeon et al., Eur. J. Immunol. 1990. 20: 1741-1745 Human natural killer cells and mature T lymphocytes express identical CD3 < subunits as defined by cDNA cloning and sequence analysis.

GuestThe Role of Extracellular Spacer Regions in the Optimal Design of Chimeric Immune Receptors J Immunother. 2005; 28:203-211.

* cited by examiner

SEQUENCE LISTING

```
Sequence total quantity: 10
SEQ ID NO: 1          moltype = AA  length = 227
FEATURE               Location/Qualifiers
source                1..227
                      mol_type = protein
```

```
                      organism = Homo sapiens
SEQUENCE: 1
MAVRRDSVWK YCWGVLMVLC RTAISKSIVL EPIYWNSSNS KFLPGQGLVL YPQIGDKLDI    60
ICPKVDSKTV GQYEYYKVYM VDKDQADRCT IKKENTPLLN CAKPDQDIKF TIKFQEFSPN   120
LWGLEFQKNK DYYIISTSNG SLEGLDNQEG GVCQTRAMKI LMKVGQDASS AGSTRNKDPT   180
RRPELEAGTN GRSSTTSPFV KPNPGSSTDG NSAGHSGNNI LGSEVAL               227

SEQ ID NO: 2          moltype = AA  length = 333
FEATURE               Location/Qualifiers
source                1..333
                      mol_type = protein
                      organism = Homo sapiens
SEQUENCE: 2
MAVRRDSVWK YCWGVLMVLC RTAISKSIVL EPIYWNSSNS KFLPGQGLVL YPQIGDKLDI    60
ICPKVDSKTV GQYEYYKVYM VDKDQADRCT IKKENTPLLN CAKPDQDIKF TIKFQEFSPN   120
LWGLEFQKNK DYYIISTSNG SLEGLDNQEG GVCQTRAMKI LMKVGQDASS AGSTRNKDPT   180
RRPELEAGTN GRSSTTSPFV KPNPGSSTDG NSAGHSGNNI LGSEVALFAG IASGCIIFIV   240
IIITLVVLLL KYRRRHRKHS PQHTTTLSLS TLATPKRSGN NNGSEPSDII IPLRTADSVF   300
CPHYEKVSGD YGHPVYIVQE MPPQSPANIY YKV                              333

SEQ ID NO: 3          moltype = DNA  length = 1356
FEATURE               Location/Qualifiers
misc_feature          1..1356
                      note = EPHB4-CAR gene
source                1..1356
                      mol_type = other DNA
                      organism = synthetic construct
SEQUENCE: 3
atggctgtga gaagggactc cgtgtggaag tactgctggg gtgttttgat ggttttatgc    60
agaactgcga tttccaaatc gatagtttta gagcctatct attggaattc ctcgaactcc   120
aaatttctac ctggacaagg actggtacta tacccacaga taggagacaa attggatatt   180
atttgcccca agtgggactc taaaactgtt ggccagtatg aatattataa agtttatatg   240
gttgataaag accaagcaga cagatgcact attaagaagg aaaataccccc tctcctcaac   300
tgtgccaaac cagaccaaga tatcaaattc accatcaaat tcaagaatt cagccctaac   360
ctctggggtc tagaatttca gaagaacaaa gattattaca ttatatctac atcaaatggg   420
tctttggagg gcctggataa ccaggaggga ggggtgtgcc agacaagagc catgaagatc   480
ctcatgaaag ttggacaaga tgcaagttct gctggatcaa ccaggaataa agatccaaca   540
agacgtccag aactagaagc tggtacaaat ggaagaagt cgacaacaag tccctttgta   600
aaaccaaatc caggttctag cacagacggc aacagcgccg gacattcggg gaacaacatc   660
ctcggttccg aagtggcctt atcctcagcg gccgcaattg aagttatgta tcctcctcct   720
tacctagaca atgagaagag caatggaacc attatccatg tgaaagggaa acacctttgt   780
ccaagtcccc tatttcccgg accttctaag cccttttggg tgctggtggt ggttggggga   840
gtcctggctt gctatagctt gctagtaaca gtggcctttta ttattttctg ggtgaggag   900
aagaggagca ggctcctgca cagtgactac atgaacatga ctccccgccg ccccgggccc   960
acccgcaagc attaccagcc ctatgcccca ccacgcgact cgcagcctta cgctccaga  1020
gtgaagttca gcaggagcgc agacgccccc gcgtaccagc agggccagaa ccagctctat  1080
aacgagctca atctaggacg aagagaggag tacgatgttt tggacaagag acgtggccgg  1140
gaccctgaga tggggggaaa gccgagaagg aagaaccctc aggaaggcct gtacaatgaa  1200
ctgcagaaag ataagatggc ggaggcctac agtgagattg gatgaaagg cgagcgccgg  1260
agggggcaagg ggcacgatgg cctttaccag ggtctcagta cagccaccaa ggacacctac  1320
gacgcccttc acatgcaggc cctgccccct cgctaa                          1356

SEQ ID NO: 4          moltype = DNA  length = 5660
FEATURE               Location/Qualifiers
source                1..5660
                      mol_type = other DNA
                      organism = synthetic construct
SEQUENCE: 4
tcgagatggc tgtgagaagg gactccgtgt ggaagtactg ctggggtgtt ttgatggttt    60
tatgcagaac tgcgatttcc aaatcgatag ttttagagcc tatctattgg aattcctcga   120
actccaaatt tctacctgga caaggactgg tactataccc acagatagga gacaaattgg   180
atattatttg ccccaaagtg gactctaaaa ctgttggcca gtatgaatat tataaagttt   240
atatggttga taaagaccaa gcagacagat gcactattaa gaaggaaaat acccctctcc   300
tcaactgtgc caaaccagac caagatatca aattcagcc cagtttcaa gaattcagcc   360
ctaacctctg gggtctagaa tttcagaaga caaagatta ttacattata tctcatcaa   420
atgggtcttt ggagggcctg ataaccagg agggaggggt gtgccagaca gagccatga   480
agatcctcat gaaagttgga caagatgcaa gttctgctgg atcaaccagg aataaagatc   540
caacaagacg tccagaacta gaagctggta caaatggaag aagttcgaca acaagtcgt   600
ttgtaaaacc aaatccaggt tctagcacag acggcaaca gcgccggacat tcggggaaca   660
acatcctcgg ttccgaagtg gccttatcct cagcggccgc aattgaagtt atgtatcctc   720
ctccttacct agacaatgag aagagcaatg gaaccattat ccatgtgaaa gggaaacacc   780
tttgtccaag tcccctattt cccggacctt ctaagccctt tgggtgctg gtggtggttg   840
ggggagtcct ggcttgctat agcttgctag taacagtggc ctttattatt ttctgggtga   900
ggagagag aggctcctgc cacagtgact acatgaacat gactccccgc cgccccgggc   960
ccacccgcaa gcattacagc cctatgcccc accacgcgac ttcgcagcct tacgct   1020
ccagagtgaa gttcagcagg agcgcagacg cccccgcgta ccagcagggc cagaaccagc  1080
tctataacga gctcaatcta ggacgaagag aggagtacga tgttttggac aagagacgtg  1140
gccgggaccc tgagatgggg ggaaagccga agaggaagaa ccctcaggaa ggcctgtaca  1200
atgaactgca gaaagataag atggcggagg cctacagtga gattggggatg aaaggcgagc  1260
```

```
gccggaggg  caaggggcac  gatggccttt  accagggtct  cagtacagcc  accaaggaca  1320
cctacgacgc  ccttcacatg  caggccctgc  cccctcgcta  aggtaccggt  tgttaacgtt  1380
agccggctac  gtatactccg  gaatattaat  aggcctagga  tgcatatggc  ggccgcttcc  1440
ctttagtgag  ggttaatgct  tcgagcagac  atgataagat  acattgatga  gtttggacaa  1500
accacaacta  gaatgcagtg  aaaaaaatgc  tttatttgtg  aaatttgtga  tgctattgct  1560
ttatttgtaa  ccattataag  ctgcaataaa  caagttaaca  acaacaattg  cattcatttt  1620
atgtttcagg  ttcagggggga  gatgtgggag  gtttttttaaa  gcaagtaaaa  cctctacaaa  1680
tgtggtaaaa  tccgataagg  atcgatccgg  gctggcgtaa  tagcgaagag  gcccgcaccg  1740
atcgccttc  ccaacagttg  cgcagcctga  atggcgaatg  gacgcgccct  gtagcggcgc  1800
attaagcgcg  gcgggtgtgg  tggttacgcg  cagcgtgacc  gctacacttg  ccagcgccct  1860
agcgcccgct  cctttcgctt  tcttcccttc  ctttctcgcc  acgttcgccc  gatagcgata  1920
aggatccgcg  tatggtgcac  tctcagtaca  atctgctctg  atgccgcata  gttaagccag  1980
ccccgacacc  cgccaacacc  cgctgacgcg  ccctgacggg  cttgtctgct  cccggcatcc  2040
gcttacagac  aagctgtgac  cgtctccggg  attttgttac  tttatagaag  aaattttgag  2100
ttttttgtttt  tttttaataa  ataaatataaac  ataaataaat  tgtttgttga  atttattatt  2160
agtatgtaag  tgtaaatata  ataaaactta  atatctattc  aaattaataa  ataaacctcg  2220
atatacagac  cgataaaaca  catgcgtcaa  ttttacgcat  gattatcttt  aacgtacgtc  2280
acaatatgat  tatctttcta  gggttaatcc  gggagctgca  tgtgtcagag  gttttcaccg  2340
tcatcaccga  aacgcgcgag  acgaaagggc  ctcgtgatac  gcctattttt  ataggttaat  2400
gtcatgataa  taatggtttc  ttagacgtca  ggtggcactt  ttcggggaaa  tgtgcgcgga  2460
accctattt  gtttattttt  ctaaatacat  tcaaatatgt  atccgctcat  gagacaataa  2520
ccctgataaa  tgcttcaata  atattgaaaa  aggaagagta  tgagtattca  acatttccgt  2580
gtcgccctta  ttcccttttt  tgcggcattt  tgccttcctg  tttttgctca  cccagaaacg  2640
ctggtgaaag  taaaagatgc  tgaagatcag  ttgggtgcac  gagtgggtta  catcgaactg  2700
gatctcaaca  gcggtaagat  ccttgagagt  tttcgccccg  aagaacgttt  tccaatgatg  2760
agcactttta  aagttctgct  atgtggcgcg  gtattatccc  gtattgacgc  cgggcaagag  2820
caactcggtc  gccgcataca  ctattctcag  aatgacttgg  ttgagtactc  accagtcaca  2880
gaaaagcatc  ttacggatgg  catgacagta  agagaattat  gcagtgctgc  cataaccatg  2940
agtgataaca  ctgcggccaa  cttacttctg  acaacgatcg  gaggaccgaa  ggagctaacc  3000
gcttttttgc  acaacatggg  ggatcatgta  actcgccttg  atcgttggga  accggagctg  3060
aatgaagcca  taccaaacga  cgagcgtgac  accacgatgc  ctgtagcaat  ggcaacaacg  3120
ttgcgcaaac  tattaactgg  cgaactactt  actctagctt  cccggcaaca  attaatagac  3180
tggatggagg  cggataaagt  tgcaggacca  cttctgcgct  cggcccttcc  ggctggctgg  3240
tttattgctg  ataaatctgg  agccggtgag  cgtgggtcct  gcggtatcat  tgcagcactg  3300
gggccagatg  gtaagccctc  ccgtatcgta  gttatctaca  cgacggggag  tcaggcaact  3360
atggatgaac  gaaatagaca  gatcgctgag  ataggtgcct  cactgattaa  gcattggtaa  3420
ctgtcagacc  aagtttactc  atatatactt  tagattgatt  taaaacttca  tttttaattt  3480
aaaaggatct  aggtgaagat  cctttttgat  aatctcatga  ccaaaatccc  ttaacgtgag  3540
ttttcgttcc  actgagcgtc  agaccccgta  gaaaagatca  aaggatcttc  ttgagatcct  3600
ttttttctgc  gcgtaatctg  ctgcttgcaa  acaaaaaaac  caccgctacc  agcggtggtt  3660
tgtttgccgg  atcaagagct  accaactctt  tttccgaagg  taactggctt  cagcagagcg  3720
cagataccaa  atactgttct  tctagtgtag  ccgtagttag  gccaccactt  caagaactct  3780
gtagcaccgc  ctacatacct  cgctctgcta  atcctgttac  cagtggctgc  tgccagtggc  3840
gataagtcgt  gtcttaccgg  gttggactca  agacgatagt  taccggataa  ggcgcagcgg  3900
tcgggctgaa  cggggggttc  gtgcacacag  cccagcttgg  agcgaacgac  ctacaccgaa  3960
ctgagatacc  tacagcgtga  gctatgagaa  agcgccacgc  ttcccgaagg  gagaaaggcg  4020
gacaggtatc  cggtaagcgg  cagggtcgga  acaggagagc  gcacgaggg  gcttccaggg  4080
ggaaacgcct  ggtatcttta  tagtcctgtc  gggtttcgcc  acctctgact  tgagcgtcga  4140
tttttgtgat  gctcgtcagg  ggggcggagc  ctatggaaaa  acgccagcaa  cgcggccttt  4200
ttacggttcc  tggccttttg  ctggcctttt  gctcacatgg  ctcgacagat  ctttaaccct  4260
agaaagatag  tctgcgtaaa  attgacgcat  gcattcttga  aatattgctc  tctctttcta  4320
aatagcgcga  atccgtcgct  gtgcatttag  gacatctcag  tcgccgcttg  gagctcccgt  4380
gaggcgtgct  tgtcaatgcg  gtaagtgtca  ctgattttga  actataacga  ccgcgtgagt  4440
caaaatgacg  catgattatc  ttttacgtga  ctttttaagat  ttaactcata  cgataattat  4500
attgttattt  tatgttctac  ttacgtgata  acttattata  tatatatttt  cttgttatag  4560
ataagatctt  caatattggc  cattagccat  attattcatt  ggttatatag  cataaatcaa  4620
tattggctat  tggccattgc  atacgttgta  tctatatcat  aatatgtaca  tttatattgg  4680
ctcatgtcca  atatgaccgc  catgttggca  ttgattattg  actagttatt  aatagtaatc  4740
aattacgggg  tcattagttc  atagcccata  tatggagttc  cgcgttacat  aacttacggt  4800
aaatggcccg  cctggctgac  cgcccaacga  ccccgccca  ttgacgtcaa  taatgacgta  4860
tgttcccata  gtaacgccaa  tagggacttt  ccattgacgt  caatgggtgg  agtatttacg  4920
gtaaactgcc  cacttggcag  tacatcaagt  gtatcatatg  ccaagtccgc  ccctattga  4980
cgtcaatgac  ggtaaatggc  ccgcctggca  ttatgcccag  tacatgacct  tacgggactt  5040
tcctacttgg  cagtacatct  acgtattagt  catcgctatt  accatggtga  tgcggttttg  5100
gcagtacacc  aatgggcgtg  gatagcggtt  tgactcacgg  ggatttccaa  gtctccaccc  5160
cattgacgtc  aatgggagtt  tgttttggca  ccaaaatcaa  cgggactttc  caaaatgtcg  5220
taacaactgc  gatcgcccgc  cccgttgacg  caaatgggcg  gtaggcgtgt  acggtgggag  5280
gtctatataa  gcagagctcg  tttagtgaac  cgtcagatca  ctagaagctt  tattgcggta  5340
gtttatcaca  gttaaattgc  taacgcagtc  agtgcttctg  acacaacagt  ctcgaactta  5400
agctgcagtg  actctcttaa  ggtagccttg  cagaagttgg  tcgtgaggca  ctgggcaggt  5460
aagtatcaag  gttacaagac  aggtttaagg  agaccaatag  aaactgggct  tgtcgagaca  5520
gagaagactc  ttgcgtttct  gataggcacc  tattggtctt  actgacatcc  actttgcctt  5580
tctctccaca  ggtgtccact  cccagttcaa  ttacagctct  taaggctaga  gtacttaata  5640
cgactcacta  taggctagcc                                              5660
```

SEQ ID NO: 5           moltype = DNA  length = 681
FEATURE                Location/Qualifiers
source                 1..681
                       mol_type = other DNA -continued

```
                        organism = Homo sapiens
SEQUENCE: 5
atggctgtga gaagggactc cgtgtggaag tactgctggg gtgtttttgat ggttttatgc   60
agaactgcga tttccaaatc gatagttta gagcctatct attggaattc ctcgaactcc   120
aaatttctac ctggacaagg actggtacta tacccacaga taggagacaa attggatatt   180
atttgcccca aagtggactc taaaactgtt ggccagtatg aatattataa agtttatatg   240
gttgataaag accaagcaga cagatgcact attaagaagg aaaataccc tctcctcaac   300
tgtgccaaac cagaccaaga tatcaaattc accatcaagt ttcaagaatt cagccctaac   360
ctctggggtc tagaatttca gaagaacaaa gattattaca ttatatctac atcaaatggg   420
tctttggagg gcctggataa ccaggaggga ggggtgtgcc agacaagagc catgaagatc   480
ctcatgaaag ttgacaaga tgcaagttct gctggatcaa ccaggaataa agatccaaca   540
agacgtccag aactagaagc tggtacaaat ggaagaagtt cgacaacaag tccctttgta   600
aaaccaaatc caggttctag cacagacggc aacagcgccg gacattcggg gaacaacatc   660
ctcggttccg aagtggcctt a                                            681

SEQ ID NO: 6            moltype = DNA   length = 15
FEATURE                 Location/Qualifiers
source                  1..15
                        mol_type = other DNA
                        organism = synthetic construct
SEQUENCE: 6
tcctcagcgg ccgca                                                   15

SEQ ID NO: 7            moltype = DNA   length = 321
FEATURE                 Location/Qualifiers
source                  1..321
                        mol_type = other DNA
                        organism = Homo sapiens
SEQUENCE: 7
attgaagtta tgtatcctcc tccttaccta gacaatgaga agagcaatgg aaccattatc   60
catgtgaaag ggaaacacct ttgtccaagt cccctatttc ccggaccttc taagcccttt   120
tgggtgctgg tggtggttgg gggagtcctg gcttgctata gcttgctagt aacagtggcc   180
tttattattt tctgggtgag gagtaagagg agcaggctcc tgcacagtga ctacatgaac   240
atgactcccc gccgccccgg gcccacccgc aagcattacc agccctatgc cccaccacgc   300
gacttcgcag cctatcgctc c                                            321

SEQ ID NO: 8            moltype = DNA   length = 339
FEATURE                 Location/Qualifiers
source                  1..339
                        mol_type = other DNA
                        organism = Homo sapiens
SEQUENCE: 8
agagtgaagt tcagcaggag cgcagacgcc cccgcgtacc agcagggcca gaaccagctc   60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac caggtctca gtacagccac caaggacacc   300
tacgacgccc ttcacatgca ggccctgccc cctcgctaa                         339

SEQ ID NO: 9            moltype = DNA   length = 24
FEATURE                 Location/Qualifiers
source                  1..24
                        mol_type = other DNA
                        organism = synthetic construct
SEQUENCE: 9
atctcgagat ggctgtgaga aggg                                         24

SEQ ID NO: 10           moltype = DNA   length = 27
FEATURE                 Location/Qualifiers
source                  1..27
                        mol_type = other DNA
                        organism = synthetic construct
SEQUENCE: 10
atcctcagca taaggccact tcggaac                                      27
```

CHIMERIC ANTIGEN RECEPTOR GENE-MODIFIED LYMPHOCYTE HAVING CYTOCIDAL EFFECT

SEQUENCE LISTING

The instant application contains a Sequence Listing which has been submitted in XML format via EFS-Web and is hereby incorporated by reference in its entirety. The XML copy, created on Feb. 10, 2023, is named P20-544US5 Seq Listing.xml and is 18,814 bytes in size.

TECHNICAL FIELD

The present invention relates to a gene-modified lymphocyte that expresses a chimeric antigen receptor (CAR) (CAR gene-introduced lymphocyte). In particular, the present invention relates to a chimeric antigen receptor gene-modified lymphocyte capable of exerting a cytocidal effect on a highly EPHB4 receptor (Ephrin type-B receptor 4) expressing tumor, use thereof, and the like. The present application claims priority based on Japanese Patent Application No. 2016-242054 filed on Dec. 14, 2016, the entire contents of which are incorporated herein by reference.

BACKGROUND ART

In order to recover the tumor immune mechanism of cancer patients, there has been developed, in recent years, treatment with gene-modified chimeric antigen receptor (CAR) T cells (CAR-T therapy) in which genetic modification is added to T cell receptors (TCRs) possessed by cytotoxic T cells (CTLs) to allow the CTLs to directly and selectively recognize tumor cells, thereby exerting an antitumor effect (see, for example, NPL 1). CAR is a generic term for proteins having a protein that specifically recognizes a tumor antigen (usually, a single-chain antibody (scFv) having an antibody variable region modified to a single-chain amino acid sequence is used) on the N-terminal side and a T cell receptor ζ chain on the C-terminal side. CAR-expressing T cells (CAR-T cells) recognize the tumor antigen in the extracellular domain, and subsequently transmit the signal into the T cells through the ζ chain to activate the T cells, and release cytocidal factors such as perforin and granzymes to exert an antitumor effect (see, for example, NPL 1).

Cancer treatment using CAR-T cells has already been applied as a clinical trial. In the hematologic tumor area, phase 3 clinical trials were conducted for CD19-positive B-lymphoid tumors. Specifically, the trials targeted for patients with relapsed acute lymphocytic leukemia. As a result of introducing CD19-specific CAR genes into T cells collected from the patients, culturing and proliferating the cells, and infusing them into the patients' bodies, molecular biological remission in the bone marrow was obtained in all 5 cases (see, for example, NPL 2).

CITATION LIST

Non Patent Literature

[NPL 1] Eshhar Z, Waks T, Gross G, Schindler D G. Specific activation and targeting of cytotoxic lymphocytes through chimeric single-chains consistent with antibody-binding domains and the gamma or zeta subunits of the immunoglobulins and T-cell receptors. Proc Natl Acad Sci USA. 1993; 90:720-724.

[NPL 2] Brentjens R J, Davila M L, Riviere I, Park J, Wang X, Cowell L G, Bartido S, Stefanski J, Taylor C, Olszewska M, Borquez-Ojeda O, Qu J, Wasielewska T, He Q, Bernal Y, Rijo I V, Hedvat C, Kobos R, Curran K, Steinherz P, Jurcic J, Rosenblat T, Maslak P, Frattini M, Sadelain M. CD19-targeted T cells rapidly induce molecular remissions in adults with chemotherapy-refractory acute Leukemia. Sci Transl Med. 2013; 5: 177ra38.

[NPL 3] Louis C U, Savoldo B, Dotti G, Pule M, Yvon E, Myers G D, Rossig C, Russell H V, Diouf O, Liu E, Liu H, Wu M F, Gee A P, Mei Z, Rooney C M, Heslop H E, Brenner M K. Antitumor activity and long-term fate of chimeric antigen receptor-positive T cells in patients with neuroblastoma. Blood. 2011; 118:6050-6056.

[NPL 4] Ahmed N, Brawley V S, Hegde M, Robertson C, Ghazi A, Gerken C, Liu E, Dakhova O, Ashori A, Corder A, Gray T, Wu M F, Liu H, Hicks J, Rainusso N, Dotti G, Mei Z, Grilley B, Gee A, Rooney C M, Brenner M K, Heslop H E, Wels W S, Wang L L, Anderson P, Gottschalk S. Human Epidermal Growth Factor Receptor 2 (HER2)-Specific Chimeric Antigen Receptor-Modified T Cells for the Immunotherapy of HER2-Positive Sarcoma. J Clin Oncol. 2015; 33:1688-1696.

[NPL 5] Abate-Daga D, Davila M L CAR models: next-generation CAR modifications for enhanced T-cell function. Mol Ther-Oncolytics 2016; 3; 16014

[NPL 6] Gerety S S, Wang H U, Chen Z F, Anderson D J. Symmetrical mutant phenotypes of the receptor EphB4 and its specific transmembrane ligand ephrin-B2 in cardiovascular development. Mol. Cell. 1999; 4; 403-14.

[NPL 7] Lv J, Xia Q, Wang J, Shen Q, Zhang J, Zhou X. EphB4 promotes the proliferation, invasion, and angiogenesis of human colorectal cancer. Exp Mol Pathol. 2016; 100; 402-8.

[NPL 8] Pradeep S, Huang J, Mora E M, Nick A M, Cho M S, Wu S Y, Noh K, Pecot C V, Rupaimoole R, Stein M A, Brock S, Wen Y, Xiong C, Gharpure K, Hansen J M, Nagaraja A S, Previs R A, Vivas-Mejia P, Han H D, Hu W, Mangala L S, Zand B, Stagg L J, Ladbury J E, Ozpolat B, Alpay S N, Nishimura M, Stone R L, Matsuo K, Armaiz-Pena G N, Dalton H J, Danes C, Goodman B, Rodriguez-Aguayo C, Kruger C, Schneider A, Haghpeykar S, Jaladurgam P, Hung M C, Coleman R L, Liu J, Li C, Urbauer D, Lopez-Berestein G, Jackson D B, Sood A K. Erythropoietin Stimulates Tumor Growth via EphB4. Cancer Cell. 2015; 28; 610-22.

[NPL 9] Ferguson B D, Tan Y H, Kantet R S, Liu R, Gayed M J, Vokes E E, Ferguson M K, Iafrate A J, Gill P S, Salgia R. Novel EPHB4 Receptor Tyrosine Kinase Mutations and Kinomic Pathway Analysis in Lung Cancer. Sci Rep. 2015; 5; 10641.

[NPL 10] Becerikli M, Merwart B, Lam M C, Suppelna P, Rittig A, Mirmohammedsadegh A, Stricker I, Theiss C, Singer B B, Jacobsen F, Steinstraesser L. EPHB4 tyrosine-kinase receptor expression and biological significance in soft tissue sarcoma. Int J Cancer. 2015; 136; 1781-91.

[NPL 11] Mertens-Walker I, Lisle J E, Nyberg W A, Stephens C R, Burke L, Rutkowski R, Herington A C, Stephenson S A. EphB4 localises to the nucleus of prostate cancer cells. Exp Cell Res. 2015; 333; 105-15.

[NPL 12] Ferguson B D, Tretiakova M S, Lingen M W, Gill P S, Salgia R. Expression of the EPHB4 receptor tyrosine kinase in head and neck and renal malignancies-implications for solid tumors and potential for therapeutic inhibition. Growth Factors. 2014; 32; 202-6.

[NPL 13] Aslam M I, Abraham J, Mansoor A, Druker B J, Tyner J W, Keller C. PDGFRB reverses EphB4 signaling in alveolar rhabdomyosarcoma. Proc Natl Acad Sci USA. 2014; 111; 6383-8.

[NPL 14] Schmitt F, Nguyen P H, Gupta N, Mayer D. Eph receptor B4 is a regulator of estrogen receptor alpha in breast cancer cells. J Recept Signal Transduct Res. 2013; 33; 244-8.

[NPL 15] Ferguson B D, Liu R, Rolle C E, Tan Y H, Krasnoperov V, Kanteti R, Tretiakova M S, Cervantes G M, Hasina R, Hseu R D, Iafrate A J, Karrison T, Ferguson M K, Husain A N, Faoro L, Vokes E E, Gill P S, Salgia R. The EphB4 receptor tyrosine kinase promotes lung cancer growth: a potential novel therapeutic target. PLOS One. 2013; 8; e67668.

[NPL 16] Liu R, Ferguson B D, Zhou Y, Naga K, Salgia R, Gill P S, Krasnoperov V. EphB4 as a therapeutic target in mesothelioma. BMC Cancer. 2013; 13; 269.

[NPL 17] Li M, Zhao Z. Clinical implications of EphB4 receptor expression in pancreatic cancer. Mol Biol Rep. 2013; 40; 1735-41.

[NPL 18] Hasina R, Mollberg N, Kawada I, Mutreja K, Kanade G, Yala S, Surati M, Liu R, Li X, Zhou Y, Ferguson B D, Nallasura V, Cohen K S, Hyjek E, Mueller J, Kanaseti R, El Hashani E, Kane D, Shimada Y, Lingen M W, Husain A N, Posner M C, Waxman I, Villaflor V M, Ferguson M K, Varticovski L, Vokes E E, Gill P, Salgia R. Critical role for the receptor tyrosinese kinase EPHB4 in esophageal cancers. Cancer Res. 2013; 73; 184-94.

[NPL 19] Rutkowski R, Mertens-Walker I, Lisle J E, Herington A C, Stephenson S A. Evidence for a dual function of EphB4 as tumor promoter and suppressor regulated by the absence or presence of the ephrin-B2 ligand. Int J Cancer; 2012; 131; E614-24.

[NPL 20] Noren N K1, Foos G, Hauser C A, Pasquale E B. The EphB4 receptor suppresses breast cancer cells tumorigenicity through an Abl-Crk pathway. Nat Cell Biol. 2006; 8; 815-25.

[NPL 21] Aitsebaomo J1, Portbury A L, Schisler J C, Patterson C. Brothers and sisters: molecular insights into arterial-venous heterogeneity. Circ Res. 2008; 103; 929-39.

[NPL 22] Boyd A W, Bartlett P F, Lackmann M. Therapeutic targeting of EPH receptors and their ligands. Nat Rev Drug Discovery 2014; 1339-62.

SUMMARY OF INVENTION

Technical Problem

Although CAR-T cell therapies for neuroblastoma and osteosarcoma are being developed in the solid tumor area (NPL 3 and NPL 4), sufficient research has not been made yet, nor has clinical application been conducted. Therefore, an object of the present invention is to provide a therapeutic strategy in the solid tumor area and a means useful therefor to further advance the clinical application of CAR therapy.

Solution to Problem

In order to cause CAR-T cells to specifically and potently act on tumor cells, (1) identification of cancer antigens which are highly expressed only in tumors and can be targeted by CAR-T cells, (2) identification and cloning of molecules specifically binding to the cancer antigens are important (see, for example, NPL 5). The present inventors have focused on an EPHB4 receptor in advancing the study in consideration of this point. EPHB4 is a member of the Eph family of receptor tyrosine kinases. In embryonic development, the binding, to EPHB4, of EphrinB2 as its ligand plays an important role in the regulation of cell adhesion and cell movement and in the development of blood vessels (see NPL 6). Furthermore, the inappropriate function of the Eph receptor may cause malignancy, as tissue breakdown and abnormal cell adhesion, movement and survival are features that are shown at advanced stages of cancer. In fact, it has been reported that EPHB4 is highly expressed in various cancers such as lung cancer, bowel cancer, malignant mesothelioma, esophagus cancer, breast cancer, and rhabdomyosarcoma, and is involved in malignant transformation of cancer. (See NPLs 7 to 20). In addition, it has been shown that the proliferation of these tumor cells is markedly suppressed by the ephrinB2-Fc molecule that selectively blocks the function of EPHB4 (see NPL 20). Furthermore, although EPHB4 is partially expressed weakly in vascular endothelial cells, the expression in other normal tissues is extremely low (see NPL 21). In addition, no significant adverse events were observed in clinical trials involving application of an EphB4 inhibitor, EPHB4-HSA, to malignant tumor patients (see NPL 22). Interestingly, it has been revealed that the activation of EPHB4 in cancer malignant transformation occurs in a ligand-independent manner, and that the ligand-dependent activation of EPHB4 (activation of EPHB4 by binding of EphrinB2 to EPHB4) in cancer cells induces cell death in cancer cells (see NPLs 13 and 20).

According to the above observation, EPHB4 is considered to be a promising cancer antigen, i.e., a "therapeutic target", in tumors that highly express EPHB4. Therefore, the present inventors have arrived at the idea that tumor cells that highly express EPHB4 can be specifically attacked by constructing a gene-modified T cell that specifically recognizes EPHB4. Since EPHB4 is a receptor, its ligand EphrinB2 can specifically and potently bind to EPHB4. It is considered that the incorporation of the binding site (extracellular domain) to EPHB4 in EphrinB2 into a chimeric antigen receptor (CAR) can construct a gene-modified T cell which specifically recognizes an EPHB4 expressing tumor cell and having a cytocidal effect. Furthermore, it is considered that, since only the binding between a CAR having an EphrinB2 extracellular domain and EPHB4 alone is also expected to induce cell death, the CAR has a therapeutic effect higher than that of a CAR using a conventional antibody variable region and is more ideal.

Based on the above idea, an EPHB4-targeted CAR vector (EPHB4-CAR vector) in which a gene encoding EphrinB2 (EFNB2) extracellular domain is inserted into a CAR expression vector has been constructed to prepare a gene-modified T cell (EPHB4-CAR-T cell). It is considered that the use of the EphrinB2 extracellular domain as an EPHB4 recognition site of a CAR can be expected to provide both of a cell death induction effect on cancer cells by EphrinB2-EPHB4 binding and a cytocidal effect of the CAR-T cell, which are not observed in conventional single-chain antibody type CARs. In fact, as a result of study on the properties and effects of EPHB4-CAR-T cells, it has been proved that a tumor highly expressing EPHB4 and EPHA2 can be killed. That is, the effectiveness of the strategy created by the present inventors has been confirmed by experiments.

Based on the above results, the following inventions are provided.

[A] A chimeric antigen receptor comprising an extracellular domain including an EphrinB2 extracellular domain, a transmembrane domain, and an intracellular signal domain for the effector function of immunocytes.

[B] The chimeric antigen receptor according to [A], wherein the EphrinB2 extracellular domain comprises an amino acid sequence of SEQ ID NO: 1.

[C] The chimeric antigen receptor according to [A] or [B], wherein the intracellular signal domain includes the intracellular domain of a costimulatory molecule and CD3ζ.

[D] The chimeric antigen receptor according to [C], wherein the costimulatory molecule is CD28.

[E] The chimeric antigen receptor according to any one of [A] to [D], comprising a spacer domain between the extracellular domain and the transmembrane domain.

[F] A polynucleotide encoding the chimeric antigen receptor according to any one of [A] to [E].

[G] A method for preparing a gene-modified lymphocyte expressing a chimeric antigen receptor, comprising a step of introducing the gene according to [F] into a target cell.

[H] The preparation method according to [G], wherein the introduction of the gene is carried out by a transposon method.

[I] The preparation method according to [H], wherein the transposon method is the piggyBac transposon method.

[J] The preparation method according to any one of [G] to [I], wherein the target cell is a T cell.

[K] A gene-modified lymphocyte expressing the chimeric antigen receptor according to any one of [A] to [E].

[L] The gene-modified lymphocyte according to [K], wherein the lymphocyte is a T cell.

[M] A cell preparation comprising a therapeutically effective amount of the gene-modified lymphocyte according to [K] or [L].

[N] The cell preparation according to [M] for treatment of tumor or cancer selected from the group consisting of soft tissue tumor (such as rhabdomyosarcoma), bone tumor, brain tumor (such as glioblastoma), lung cancer, bowel cancer, malignant mesothelioma, esophagus cancer, breast cancer, ovarian cancer, melanoma, and head and neck cancer.

[O] A treatment method comprising a step of administering a therapeutically effective amount of the gene-modified lymphocyte according to [K] or [L] to a patient with tumor or cancer expressing EPHB4 or EPHA2. Preferably, the tumor or cancer expressing EPHB4 is selected from the group consisting of rhabdomyosarcoma, lung cancer, bowel cancer, malignant mesothelioma, esophagus cancer, breast cancer, ovarian cancer, melanoma, and head and neck cancer, and the tumor or cancer expressing EPHA2 is selected from the group consisting of soft tissue tumor (such as rhabdomyosarcoma), bone tumor, brain tumor (such as glioblastoma), lung cancer, esophagus cancer, breast cancer, and melanoma.

[P] An expression cassette comprising a promoter and the gene according to [F] under the control of the promoter.

[Q] A vector having the expression cassette according to [P].

[R] The vector according to [Q], wherein the vector has a structure that the expression cassette is sandwiched between a pair of transposon inverted repeat sequences.

[S] A kit for preparing a gene-modified lymphocyte expressing a chimeric antigen receptor, the kit comprising the vector according to [R] and a transposase expression vector.

[T] The preparation kit according to [S], wherein the transposase is piggyBac transposase.

DESCRIPTION OF EMBODIMENTS

1. Chimeric Antigen Receptor

Figure 1:
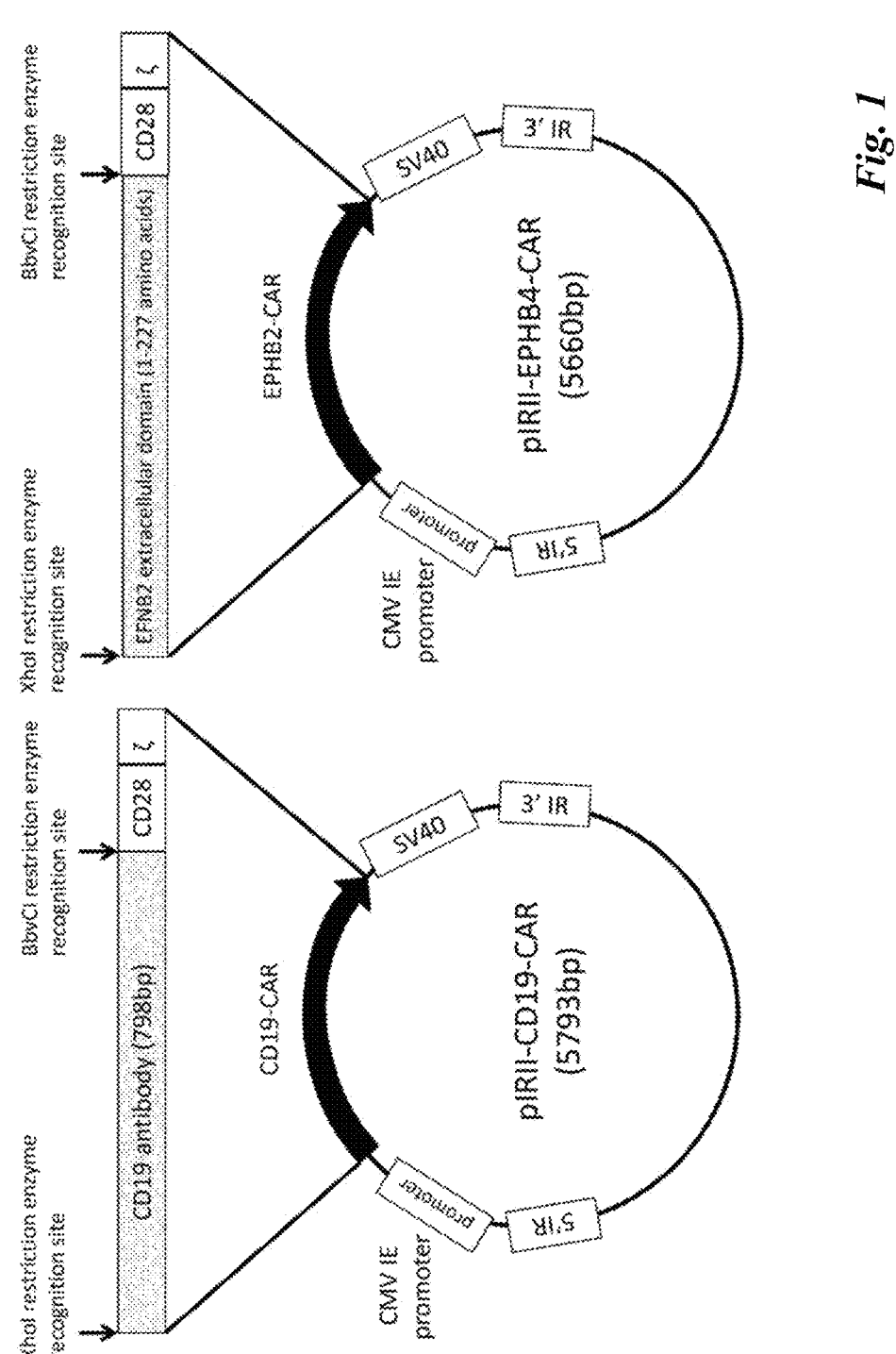
FIG. 1 shows the structure of a CAR expression piggyBac transposon vector. The left portion of FIG. 1 shows CD19-CAR expression vector (pIRII-CD19-CAR), and the right portion of FIG. 1 shows EPHB4-CAR expression vector (pIRII-EPHB4-CAR).

A first aspect of the present invention relates to a chimeric antigen receptor (the chimeric antigen receptor is referred to as "CAR" in accordance with customary practice) in which the extracellular domain of the CAR binds to EPHB4 (Ephrin type-B receptor 4). The CAR of the present invention targets EPH family protein, such as EPHB4 and EPHA2 (Ephrin type-A receptor 2). In order to exert its unique function, the CAR of the present invention has a characteristic structure. Specifically, it has an extracellular domain including an EphrinB2 extracellular domain, a transmembrane domain, and an intracellular signal domain for the effector function of immunocytes.

(a) Extracellular Domain

Common CARs utilize single-chain antibodies (scFv) that specifically recognize a target to obtain antigen specificity. In contrast, the CAR of the present invention utilizes an extracellular domain of EphrinB2 protein, which is a natural ligand of the target EPHB4, for antigen recognition. The amino acid sequence of the extracellular domain of EphrinB2 protein is shown in SEQ ID NO: 1. Typically, the extracellular domain of the CAR of the present invention is constituted by a polypeptide chain consisting of the amino acid sequence. However, the extracellular domain of the CAR of the present invention may contain a portion other than the extracellular domain of EphrinB2 protein, or alternatively, may be composed of a part of the extracellular domain of EphrinB2 protein as long as it exhibits the function, i.e., binding activity for EPHB4 and EPHA2. In addition, as long as the binding activity for EPHB4 and EPHA2 is not impaired, a part of the above amino acid sequence may be modified. The modification herein can occur by deletion, substitution, addition, and the like of amino acid residues constituting the amino acid sequence. The number of amino acids to be modified is, for example, 50 or less, preferably 25 or less, more preferably 15 or less, still more preferably 10 or less, and most preferably 5 or less.

(b) Transmembrane Domain

The transmembrane domain intervenes between the extracellular domain and intracellular signal domain. Examples of the transmembrane domain used herein include CD28, CD38, CD8a, CD3, CD4, and 4-1BB. Alternatively, a transmembrane domain composed of an artificially constructed polypeptide may be used.

(c) Intracellular Signal Domain

The intracellular signal domain transmits the signals necessary for exertion of the effector function of immunocytes. More specifically, when the extracellular domain binds with the target antigen, an intracellular signal domain capable of transmitting the signals necessary for activation of immunocytes are used. The intracellular signal domain includes the domain for transmitting the signals through the TCR complex (for convenience, referred to as "the first domain"), and the domain for transmitting the costimulatory signals (for convenience, referred to as "the second domain"). As the first domain, CD3ζ or other intracellular domains such as FcεRIγ may be used. The use of CD3ζ is preferred. As the second domain, the intracellular domain of a costimulatory molecule is used. Examples of the costimulatory molecule include CD28, 4-1BB (CD137), CD2, CD4, CD5, CD134, OX-40, and ICOS. The use of the intracellular domain of CD28 or 4-1BB is preferred.

The linking form of the first and second domains is not particularly limited, and preferably the second domain is disposed on the transmembrane domain side, because it is known that co-stimulation was strongly transmitted when CD3ζ was linked distally in a past case. The same or different kinds of plural intracellular domains may be linked in tandem to form the first domain. The same holds true for the second domain.

The first and second domains may be directly linked, or a linker may intervene between them. The linker may be, for example, a peptide linker. The peptide linker is composed of peptides which are linear chains of amino acids. The structure and characteristics of the peptide linker are as described above. However, the linker used herein may be composed solely of glycine. The length of the linker is not particularly limited. For example, a linker composed of 2 to 15 amino acid residues may be used.

(d) Other Elements

A leader sequence (signal peptide) is used to promote CAR secretion. For example, the leader sequence of the GM-CSF receptor may be used. In addition, the structure is preferably composed of an extracellular domain and a transmembrane domain linked together through a spacer domain. More specifically, the CAR according to a preferred embodiment contains a spacer domain between the extracellular domain and transmembrane domain. The spacer domain is used for promoting linking between the CAR and target antigen. For example, the Fc fragment of a human IgG (for example, human IgG1 or human IgG4) may be used as the spacer domain. Alternatively, a part of the extracellular domain of CD28 or a part of the extracellular domain of CD8a may be used as the spacer domain. A spacer domain may be placed between the transmembrane domain and intracellular signal domain.

There are some reports on the experiments and clinical studies using CARs (for example, Rossig C, et al. Mol Ther 10:5-18, 2004; Dotti G, et al. Hum Gene Ther 20:1229-1239, 2009; Ngo M C, et al. Hum Mol Genet 20 (R1): R93-99, 2011; Ahmed N, et al. Mol Ther 17:1779-1787, 2009; Pule M A, et al. Nat Med 14:1264-1270, 2008; Louis C U, et al. Blood 118:6050-6056, 2011; Kochenderfer J N, et al. Blood 116:4099-4102, 2010; Kochenderfer J N, et al. Blood 119: 2709-2720, 2012; Porter D L, et al. N Engl J Med 365:725-733, 2011; Kalos M, et al. Sci Transl Med 3: 95ra73,2011; Brentjens R J, et al. Blood 118:4817-4828, 2011; and Brentjens R J, et al. Sci Transl Med 5:177 ra38, 2013), and the CARs in the present invention may be constructed with reference to these reports.

2. Polynucleotide Encoding Chimeric Antigen Receptor (CAR) and Use Thereof

A second aspect of the present invention relates to a CAR-encoding polynucleotide (hereinafter sometimes referred to as "CAR polynucleotide") and use thereof (expression cassette, vector, method for preparing a gene-modified lymphocyte expressing the CAR, gene-modified lymphocyte expressing the CAR, and use thereof). The CAR polynucleotide of the present invention encodes a CAR having the above structure. Therefore, by introducing it into a target cell and expressing it, a gene-modified lymphocyte (CAR polynucleotide-introduced lymphocyte) expressing the CAR of the present invention on the cell surface can be obtained. The CAR polynucleotide-introduced lymphocyte can be used for CAR therapy. A specific example of the sequence of the CAR polynucleotide is shown in SEQ ID NO: 3. The CAR polynucleotide has, from the 5' end toward the 3' end, a region (SEQ ID NO: 5) encoding the EphrinB2 extracellular domain (SEQ ID NO: 1), a linker sequence (SEQ ID NO: 6), a region (SEQ ID NO: 7) encoding CD28 (including transmembrane domain and intracellular domain), and a region (SEQ ID NO: 8) encoding the CD35 intracellular domain, which are arranged in series.

An expression cassette (hereinafter may be referred to as "CAR expression cassette") can be constructed by using a CAR polynucleotide. The CAR expression cassette includes a promoter and a CAR polynucleotide under control of the promoter. Usually, the CAR polynucleotide is disposed downstream of the promote so as to be under control of the promoter. Examples of the promoter used in the CAR expression cassette include CMV-IE (cytomegalovirus early gene-derived promoter), SV40ori, retrovirus LTP, SRα, EF1α, and β actin promoter. The promoter is operably linked to the CAR polynucleotide. "The promoter is operably linked to the CAR polynucleotide." has the same meaning with "the CAR polynucleotide is disposed under control of the promoter", and usually, the CAR polynucleotide is linked to the 3' terminal side of the promoter directly or via other sequence. A poly-A additional signal sequence is disposed downstream of the CAR polynucleotide. Transcription is terminated by the use of the poly-A additional signal sequence. The poly-A additional signal sequence may be, for example, the poly-A additional sequence of SV40, or the poly-A additional sequence of a bovine-derived growth hormone gene.

The expression cassette may include, for example, a gene for detection (for example, a reporter gene, cell or tissue-specific gene, or selectable marker gene), an enhancer sequence, and a WRPE sequence. The gene for detection is used for the judgement of success/failure or efficiency of the introduction the expression cassette, detection of CAR polynucleotide expression or judgement of the expression efficiency, and selection and collection of the cells having expressed the CAR polynucleotide. On the other hand, the enhancer sequence is used for improving the expression efficiency. Examples of the gene for detection include the neo gene imparting resistance against neomycin, the npt gene (Herrera Estrella, EMBO J.2 (1983), 987-995) and npt II gene (Messing & Vierra.Gene 1 9:259-268(1982)) imparting resistance against kanamycin, the hph gene imparting resistance against hygromycin (Blochinger & Diggl mann, Mol Cell Bio 4:2929-2931), and the dhfr gene imparting resistance against Methotrexate (Bourouis et al., EMBO J.2(7)) (the aforementioned are marker genes); genes of fluorescence proteins such as the luciferase gene (Giacomin, P1.Sci.116 (1996), 59 to 72; Scikantha, J.Bact. 178 (1996), 121), the β-glucuronidase (GUS) gene, GFP (Gerdes, FEBS Lett. 389 (1996), 44-47), and their variants (EGFP and d2EGFP) (the aforementioned are reporter genes); and the epidermal growth factor receptor (EGFR) gene deficient in the intracellular domain. The gene for detection is linked to the CAR polynucleotide through, for example, a bicistronic control sequence (for example, internal ribosome entry site (IRES)) and a sequence coding a self cleavage peptide. Examples of the self cleavage peptide include, but not limited to, the 2A peptide (T2A) derived from Thosea asigna virus. Known examples of the self cleavage peptide include the 2A peptide (F2A) derived from the Foo-and-mouse disease virus (FMDV), the 2A peptide (E2A) derived from equine rhinitis A virus (ERAV), and the 2A peptide (P2A) derived from porcine teschovirus (PTV-1).

The car expression cassette is included in a vector for its delivery to a target cell. The "vector" herein refers to a nucleic acid molecule capable of delivering a nucleic acid molecule inserted therein into a target (target cell). The form thereof, the origin thereof and the like are not particularly limited. A variety of the vectors can be employed. Examples of preferred vector include a viral vector. However, non-viral vector can be used. The viral vector cleverly uses the phenomenon of the infection of a virus to a cell, and provides a high gene introduction efficiency. As the viral vectors, for example, retrovirus vector, lentivirus vector, adenovirus vector, adeno-associated virus vector, herpesvirus vector, and Sendai virus vector have been developed. Among them, the retrovirus vector, lentivirus vector, and adeno-associated virus vector are expected to achieve stable and long-term expression, because the target genes included in these vectors are integrated in the host chromosomes. These viral vectors can be prepared according to known methods, or using a commercially available kit. Examples of the non-viral vector include plasmid vector, liposome vector, positively charged liposome vector (Felgner, P. L., Gadek, T. R., Holm, M. et al., Proc. Natl. Acad. Sci., 84:7413-7417, 1987), YAC vector, and BAC vector.

The gene introduction is preferably carried out by a transposon method. The transposon method is one of the non-viral gene introduction methods. Transposon is the generic name of short gene sequences causing a gene transposition conserved during the process of evolution. A pair of a gene enzyme (transposase) and its specific recognition sequence causes gene transposition. The transposon method may be, for example, the piggyBac transposon method. The piggyBac transposon method uses the transposon isolated from insects (Fraser M J et al., Insect Mol Biol. 1996 May; 5(2): 141-51; Wilson M H et al., Mol Ther. 2007 January; 15(1): 139-45.), and allows highly efficient integration into mammal chromosomes. The piggyBac transposon method is actually used for the introduction of the CAR polynucleotide (for example, see Nakazawa Y, et al., J Immunother 32:826-836, 2009; Nakazawa Y et al., J Immunother 6:3-10, 2013). The transposon method applicable to the present invention is not limited to that using piggyBac, and may use a method using transposon, for example, Sleeping Beauty (Ivics Z, Hackett P B, Plasterk R H, Izsvak Z (1997) Cell 91:501-510.), Frog Prince (Miskey C, Izsvak Z, Plasterk R H, Ivics Z (2003) Nucleic Acids Res 31:6873-6881.), Toll (Koga A, Inagaki H, Bessho Y, Hori H. Mol Gen Genet. 1995 Dec. 10; 249 (4): 400-5; Koga A, Shimada A, Kuroki T, Hori H, Kusumi J, Kyono-Hamaguchi Y, Hamaguchi S. J Hum Genet. 2007; 52(7): 628-35.Epub 2007 Jun. 7.), To12 (Koga A, Hori H, Sakaizumi M (2002) Mar Biotechnol 4:6-11; Johnson Ha mL et M R, Yergeau D A, Kuliyev E, Takeda M, Taira M, Kawakami K, Mead P E (2006) Genesis 44:438-445; Choo B G, Kondrichin I, Parinov S, Emelyanov A, Go W, Toh W C, and Korzh V (2006) BMC Dev Biol 6:5.).

The introduction operation by the transposon method may be carried out by an ordinary method with reference to past literatures (for example, for the piggyBac transposon method, see Nakazawa Y, et al., J Immunother 32:826-836, 2009, Nakazawa Y et al., J Immunother 6:3-10, 2013, Saha S, Nakazawa Y, Huye L E, Doherty J E, Galvan D L, Rooney C M, Wilson M H. J Vis Exp. 2012 Nov. 5; (69): e4235, Saito S, Nakazawa Y, Sueki A, et al. Anti-leukemic potency of piggyBac-mediated CD19-specific T cells against refractory Philadelphia chromosome-positive acute lymphoblastic leukemia. Cytotherapy. 2014; 16:1257-69.).

In a preferred embodiment of the present invention, the piggyBac transposon method is used. Typically, in the piggyBac transposon method, a vector including the gene coding piggyBac transposase (transposase plasmid) and a vector having a structure wherein the desired nucleic acid construct (CAR expression cassette) is sandwiched between piggyBac inverted repeat sequences (transposon plasmid) are prepared, and these vectors are introduced (transfected) to the target cell. The transfection may use various methods such as electroporation, nucleofection, lipofection, or calcium phosphate method.

Examples of a target cell (the cell into which the CAR polynucleotide is introduced) include CD4-positive CD8-negative T-cells, CD4-negative CD8-positive T-cells, T-cells prepared from iPS cells, αβ-T-cells, γδ-T-cells, NK cells, and NKT cells. Various cell populations may be used, as long as they contain the above-described lymphocytes or precursor cells. PBMCs (peripheral blood mononuclear cells) collected from the peripheral blood is one of the preferred target cells. More specifically, in a preferred embodiment, gene introduction operation is carried out on the PBMCs. The PBMCs may be prepared by an ordinary method. The method for preparing the PBMCs may refer to, for example, Saha S, Nakazawa Y, Huye L E, Doherty J E, Galvan D L, Rooney C M, Wilson M H. J Vis Exp. 2012 Nov. 5; (69): e4235. Unless otherwise specified, the cells (for example, T-cells) herein are human cells.

The CAR polynucleotide-introduced lymphocytes obtained by the above steps are typically subjected to activation treatment. For example, the CAR polynucleotide-introduced lymphocytes are activated by stimulation with an anti-CD3 antibody and an anti-CD28 antibody. This treatment also usually promotes survival and proliferation of the CAR polynucleotide-introduced lymphocytes. For example, stimulation by the anti-CD3 antibody and anti-CD28 antibody can be applied by culturing in a culture vessel (for example, culture dish) coated with the anti-CD3 antibody and anti-CD28 antibody on the culture surface for 1 to 20 days, preferably 3 to 14 days, and more preferably 5 to 10 days. The anti-CD3 antibody (for example, CD3PUREantibody provided by Miltenyi Biotec) and the anti-CD28 antibody (for example, CD28pure antibody provided by Miltenyi Biotec) are readily and commercially available. Magnetic beads (for example, Dynabeads T-Activator CD3/CD28 provided by VERITAS) coated with the anti-CD3 antibody and anti-CD28 antibody may be used to apply the stimulation. The anti-CD3 antibody is preferably "OKT3" clone. In order to promote recovery from injury/disturbance by gene introduction operation, the activation treatment is preferably carried out about 8 to 48 hours (preferably 16 to 24 hours) after the gene introduction operation, rather than immediately after the gene introduction operation.

In order to improve the survival rate/proliferation rate of the cells, it is preferred to use a culture solution containing a T-cell growth factor in the activation treatment. The T-cell growth factor is preferably IL-15. Preferably, a culture solution containing IL-15 and IL-7 is used. The concentration of IL-15 is, for example, from 1 ng/mL to 20 ng/ml, and preferably from 5 ng/ml to 10 ng/mL. The concentration of IL-7 is, for example, from 1 ng/ml to 20 ng/mL, and preferably from 5 ng/mL to 10 ng/mL. The T-cell growth factor such as IL-15 or IL-7 may be prepared according to a common procedure. Alternatively, a commercial product may be used. Although the use of animal T-cell growth factors other than human ones will not be excluded, the T-cell growth factor used herein is usually derived from human (may be a recombinant). The growth factors such as human IL-15 and human IL-7 are readily available (for example, provided by Miltenyi Biotec, R&D systems).

A medium containing blood serum (for example, human blood serum or fetal bovine serum) may be used, but the use of a serum-free medium allows the preparation of cells having advantages of high safety in clinical application, and safe advantages of a high level of safety and little difference in the culture efficiency among blood serum lots. Specific example of the serum-free medium for lymphocytes include TexMACS™ (Miltenyi Biotec, GMP-grade serum-free cell culture medium) and AIM V® (Thermo Fisher Scientific, serum-free lymphocyte/T-cell culture medium). When a blood serum is used, the blood serum is preferably an autologous serum, or a blood serum collected from a patient to receive administration of CAR polynucleotide-introduced lymphocytes obtained by the preparation method of the present invention. The basal culture medium is the one suitable for culture of lymphocytes, and a specific example is the above-listed TexMACS™, AIM V®. Other culture conditions may be common ones, as long as they are suitable for the survival and proliferation of lymphocytes. For example, the lymphocytes are cultured in a CO2 incubator adjusted at 37° C. (CO2 concentration: 5%).

After activating treatment, the cells are collected. The collecting operation may follow an ordinary method. For example, the cells are collected by pipetting or centrifugation. In one preferred embodiment, before the collecting operation, the cells after activating treatment is cultured in the presence of a T-cell growth factor. This step allows efficient expanded culture, and increases the cell survival rate. The T-cell growth factor used herein may be, for example, IL-15 or IL-7. In the same manner as in the activating treatment, the cells may be cultured in a medium containing IL-15 and IL-7. The culture period is for example from 1 to 21 days, preferably from 5 to 18 days, and more preferably from 10 to 14 days. If the culture period is too short, the number of cells will not sufficiently increase, and if the culture period is too long, cell activity (survival ability) may decrease, and the cell may cause exhaustion/fatigue or the like. The cells may be subcultured during the culture. During the culture, the medium is replaced as necessary. For example, about 1/3 to 2/3 the culture solution is replaced with a new medium once in three days.

In one embodiment of the present invention, as a CAR polynucleotide-introduced lymphocyte, chimeric antigen receptor gene-modified T cells which acquired virus specificity (referred to as "virus specificity-acquired CAR-T cells") are prepared. The virus specificity-acquired CAR-T cells have important advantages in clinical application, such as their use in autotransplantation improves internal persistence by stimulation from a viral T cell receptor, and their use in allogeneic transplantation further allows the preparation of CAR-T from a transplanted donor owing to the reduction of allogeneic immunity reaction (GVHD), and creates possibility of drug formulation of CAR-T cells from a third party donor. Actually, there is a report that virus specificity-acquired CAR-T cells survive longer in the body (Pule M A, et al. Nat Med. 2008 November; 14 (11): 1264-70.). In addition, the report of a third party-derived EBV-specific CTL clinical study (Annual Review Blood 2015, published in January 2015, Chugai-Igakusha) supports high level of safety of virus specificity-acquired cytotoxic T cells (CTLs).

The preparation method of this embodiment includes the following steps (i) to (iv).

(i) A step of preparing non-proliferative cells holding a viral peptide antigen, which are obtained by stimulating a group of cells including T cells using an anti-CD3 antibody and an anti-CD28 antibody followed by culturing in the presence of the viral peptide antigen and a treatment for causing the cells to lose their proliferation capability (ii) A step of obtaining gene-modified T cells by introducing a EPHB4 receptor-specific chimeric antigen receptor gene into target cells (iii) A step of mixing the non-proliferative cells prepared by step (i) with the gene-modified T cells obtained by step (ii), and co-culturing the mixed cells (iv) A step of collecting the cells after culture.

In step (i), firstly, the group of cells including T cells are stimulated with an anti-CD3 antibody and an anti-CD28 antibody, thereby obtaining activated T cells. As the "a group of cells including T cells", preferably, PBMCs (peripheral blood mononuclear cells) collected from the peripheral blood are used. The "group of cells including T cells" herein may be, for example, the PBMCs which have been purified to increase the T-cell content, or mononuclear cells collected from the peripheral blood by pheresis.

For example, the T cells in a group of cells can be stimulated with an anti-CD3 antibody and an anti-CD28 antibody by culturing them in a culture vessel (for example, culture dish) coated with an anti-CD3 antibody and an anti-CD28 antibody on the culturing surface for three hours to three days, preferably six hours to two days, and more preferably from 12 hours to one day. The anti-CD3 antibody (for example, the trade name CD3pure antibody provided by Miltenyi Biotec may be used) and the anti-CD28 antibody (for example, the trade name CD28PURE antibody provided by Miltenyi Biotec may be used) are commercially available and are easily available. The stimulation in step (i) may be carried out using the magnetic beads coated with an anti-CD3 antibody and an anti-CD28 antibody (for example, Dynabeads T-Activator CD3/CD28 provided by VERITAS). The anti-CD3 antibody is preferably "OKT3" clone.

After obtaining the activated T cells, they are subjected to culturing in the presence of the viral peptide antigen and a treatment for causing the cells to lose their proliferation capability. As a result of this, non-proliferative "activated T cells holding a viral peptide antigen on the cell surface" (hereinafter referred to as "viral peptide-holding non-proliferative cells") are obtained. The order of culturing in the presence of the viral peptide antigen and a treatment for causing the cells to lose their proliferation capability is not particularly limited. Accordingly, the proliferation capability may be lost after culturing in the presence of the viral peptide antigen, or the cells may be cultured in the presence of the viral peptide antigen after they were caused to lose their proliferation capability. Preferably, the former order is adopted in the expectation that the intake of the viral peptide antigen would be better than before the loss of proliferation capability.

The "treatment for losing the proliferation capability" is typically irradiation, but may use a drug. The irradiation is carried out by, for example, using a γ-ray, at an intensity of 25 Gy to 50 Gy, for 15 to 30 minutes.

In order to culture the cells in the presence of the viral peptide antigen, for example, a culture medium containing the viral peptide antigen is used.

Alternatively, the viral peptide antigen may be added to the culture medium during culturing. The addition concentration of the viral peptide antigen is, for example, from 0.5 µg/mL to 1 µg/mL. The culture period is, for example, from 10 minutes to 5 hours, and preferably from 20 minutes to 3 hours. The "viral peptide antigen" in the present description means an epitope peptide or a long peptide containing an epitope which can induce cytotoxic T cells (CTLs) specific to a specific virus. Examples of the viral peptide antigen include, but not limited to, antigen peptides of adenovirus (AdV) (for example, see WO 2007015540 A1), antigen peptides of cytomegalovirus (CMV) (for example, see Japanese Unexamined Patent Application Publication No. 2002-255997, Japanese Unexamined Patent Application Publication No. 2004-242599, and Japanese Unexamined Patent Application Publication No. 2012-87126), and antigen peptides of Epstein-Barr virus (EBV) (for example, see WO 2007049737 A1, Japanese Patent Application No. 2011-177487, and Japanese Unexamined Patent Application Publication No. 2006-188513). The viral peptide antigen can be prepared by a common procedure (for example, a solution-phase synthesis method or a solid-phase synthesis method) based on the sequence information. Some viral peptide antigens are commercially available (for example, provided by Medical & Biological Laboratories Co., Ltd., Takara Bio, Inc., and Miltenyi Biotec).

One antigen peptide may be used, but usually two or more antigen peptides (an antigen peptide mixture) are used. For example, an AdV antigen peptide mixture, a CMV antigen peptide mixture, or an EBV antigen peptide mixture, or a combination of two or more of these antigen peptide mixtures (for example, a mixture of the AdV antigen peptide mixture, CMV antigen peptide mixture, and EBV antigen peptide mixture) is used. The combination of two or more antigen peptides allows obtainment of plural activated T cells having different targets (antigen peptides), which would increase the subjects (patients) to whom the CAR-T cells obtained by the preparation method of the present invention is effective (the improvement of cover rate). When determining which virus the antigen peptide to be used is derived from, the use of the CAR-T cells obtained by the preparation method of the present invention, specifically the disease and the disease state of the patient to be treated may be considered. The AdV antigen peptide mixture, CMV antigen peptide mixture, and EBV antigen peptide mixture are commercially available (for example, PepTivator® (overlapping peptide pools) AdV5 Hexon, PepTivator® CMV pp65, PepTivator® EBV EBNA-1, PepTivator®, and EBV BZLF1 provided by Miltenyi Biotec, and PepMix™ (peptide pool) Collection HCMV, PepMix™ EBV (EBNA1) provided JPT Peptide Technologies, and the like) are easily available.

Step (ii) corresponds to the gene introduction operation (introduction of the CAR polynucleotide) explained above, a variety of gene introduction methods can be employed. Preferably, a transposon method is used. Through this step, the gene-modified T cells (CAR-T cells) are obtained.

In step (iii), the non-proliferative cells (viral peptide-holding non-proliferative cells) prepared in step (i) and the gene-modified T cells obtained in step (ii) are mixed, and the mixed cells are co-cultured. As a result of this, stimulation through the costimulatory molecules by the non-proliferative cells and stimulation by the viral antigen peptide are added, whereby the virus antigen specific gene-modified T cells are activated, and their survival and proliferation are promoted.

The ratio between the number of the non-proliferative cells used for co-culturing and the number of the gene-modified T cells (the number of non-proliferative cells/the number of gene-modified T cells) is not particularly limited, and, for example, from 0.025 to 0.5.

In this step, in principle, stimulation by an anti-CD3 antibody and an anti-CD28 antibody is not applied for the purposes of, for example, selectively proliferating the virus specificity-acquired CAR-T cells, or preventing exhaustion and fatigue of the T cells by avoiding strong stimulation. On the other hand, in order to increase the survival rate/proliferation rate of the cells, it is preferred that a culture solution containing a T-cell growth factor be used during the co-culturing. The T-cell growth factor is preferably IL-15. Preferably, a culture solution containing IL-15 and IL-7 are used. The addition amount of IL-15 is, for example, from 5 ng/mL to 10 ng/ml. In the same manner, the addition amount of IL-7 is, for example, from 5 ng/ml to 10 ng/mL. The T-cell growth factor such as IL-15 or IL-7 may be prepared according to a common procedure. Alternatively, a commercial product may be used. Although the use of animal T-cell growth factors other than human ones will not be excluded, the T-cell growth factor used herein is usually derived from human (may be a recombinant). The growth factors such as human IL-15 and human IL-7 are readily available (for example, provided by Miltenyi Biotec, R&D systems).

A culture medium containing blood serum (for example, human blood serum or fetal bovine serum) may be used, but the use of a serum-free medium allows the preparation of cells having advantages of high safety in clinical application, and little difference in the culture efficiency among blood serum lots. Specific examples of the serum-free medium for T cells include TexMACS™ (Miltenyi Biotec) and AIM V® (Thermo Fisher Scientific). When a blood serum is used, the blood serum is preferably a self-blood serum, or a blood serum collected from the individual who is the origin of the gene-modified T cells obtained in step (2) (typically, the patient to receive administration of the chimeric antigen receptor gene-modified T cells obtained by the preparation method of the present invention). The basal culture medium is the one suitable for culture of T cells, and specific examples include the above-listed TexMACS™ and AIM VR. Other culture conditions may be common ones, as long as they are suitable for the survival and proliferation of T cells. For example, the culture is carried out in a $CO_2$ incubator adjusted at 37° C. ($CO_2$ concentration: 5%).

The viral peptide-holding non-proliferative cells may be added during step (iii). Alternatively, the co-cultured cells are collected, mixed with the viral peptide-holding non-proliferative cells, and then co-culturing is carried out again. These operations may be repeated twice or more times. In this manner, the improvement of the induction rate of the virus specificity-acquired CAR-T cells and the increase of the number of the virus specificity-acquired CAR-T cells are expected by carrying out plural times of the stimulation or activation using the viral peptide-holding non-proliferative cells. The viral peptide-holding non-proliferative cells used herein are prepared anew, or a portion of the preserved cells which have been prepared in step (i).

In step (iii), the period of co-culturing is, for example, from one day to 21 days, preferably from five days to 18 days, and more preferably from 10 days to 14 days. If the culture period is too short, sufficient effect cannot be obtained, and if the culture period is too long, the activity (vital force) of the cells may decrease, and the cells may be exhausted or fatigued.

Before the co-culturing with the viral peptide-holding non-proliferative cells, the gene-modified T cells obtained in step (ii) may be co-cultured with viral peptide-holding non-proliferative PBMCs (peripheral blood mononuclear cells). In this embodiment, the cells obtained by co-culturing the gene-modified T cells obtained in step (ii) with the viral peptide-holding non-proliferative PBMCs, and the viral peptide-holding non-proliferative cells prepared in step (i) are mixed, and the mixture is co-cultured. The viral peptide-holding non-proliferative PBMCs herein can be prepared by subjecting PBMCs to culturing in the presence of a viral peptide antigen and a treatment for causing them to lose their proliferation capability. Specifically, for example, PBMC isolated from the peripheral blood are irradiated, and then cultured in the presence of a viral peptide antigen, thus obtaining viral peptide-holding non-proliferative PBMCs. The number of blood collection for carrying out the present invention can be reduced by preparing viral peptide-holding non-proliferative PBMCs using a portion of the PBMCs isolated from the peripheral blood obtained by one time of blood collection, and preparing gene-modified T cells from another portion, which will bring a markedly big advantage in clinical application. In particular, when the viral peptide-holding non-proliferative cells (the cells used for the second step co-culturing) are prepared by carrying out step (i) using the remaining PBMCs, the three kinds of necessary cells, more specifically, the gene-modified T cells, viral peptide-holding non-proliferative PBMCs used for co-culturing with these cells, and the viral peptide-holding non-proliferative cells used for the second step co-culturing can be prepared by one time of blood collection, which markedly reduces the burden imposed on the patient in the treatment using the CAR-T cells obtained in the present invention.

In step (iv) following step (iii), the cells after culture are collected. The collection operation may use an ordinary method. For example, the collection is carried out by pipetting or centrifugation treatment. The step of culturing the co-cultured cells in the presence of the T-cell growth factor (expanded culturing) may be carried out between step (iii) and step (iv). For this cell expansion, viral peptide-holding non-proliferative cells may be added, or viral peptide-holding non-proliferative cells may be added during the cell expansion.

In another embodiment, the gene-modified T cells obtained by the same operation as in step (ii) are co-cultured with viral peptide-holding non-proliferative PBMCs (peripheral blood mononuclear cells), and then stimulated with an anti-CD28 antibody (an anti-CD3 antibody may be used in combination). Subsequently, after culturing (for example, expanded culturing) as necessary, the cells are recovered to obtain CAR-T cells (virus specificity-acquired CAR-T cells as the CAR gene-introduced lymphocytes of the present invention).

3. CAR Polynucleotide-Introduced Lymphocytes and Uses Thereof

The further aspect of the present invention relates to the gene-modified lymphocyte expressing chimeric antigen receptors obtained in the preparation method of the present invention (hereinafter referred to as "CAR polynucleotide-introduced lymphocytes of the present invention") and uses thereof. The CAR polynucleotide-introduced lymphocytes of the present invention can be used for treatment, prevention, or improvement of tumor/cancer (hereinafter referred to as "target diseases") in which EPH family protein, such as EPHB4 and EPHA2, are highly expressed. Examples of the target disease include rhabdomyosarcoma, lung cancer, bowel cancer, malignant mesothelioma, esophagus cancer, breast cancer, ovarian cancer, and melanoma, head and neck cancer. Preferably, the tumor or cancer expressing EPHB4 is selected from the group consisting of rhabdomyosarcoma, lung cancer, bowel cancer, malignant mesothelioma, esophagus cancer, breast cancer, ovarian cancer, melanoma, and head and neck cancer, and the tumor or cancer expressing EPHA2 is selected from the group consisting of soft tissue tumor (such as rhabdomyosarcoma), bone tumor, brain tumor (such as glioblastoma), lung cancer, esophagus cancer, breast cancer, and melanoma. "Treatment" include alleviation (moderation) of symptoms or associated symptoms characteristic to the target diseases, inhibition or retard of deterioration of symptoms. "Prevention" means prevention or retard of development/expression of diseases (disorders) or their symptoms, or decrease of the risk of development/expression. On the other hand, "improvement" means alleviation (moderation), change for the better, amelioration, or healing (containing partial healing).

The CAR polynucleotide-introduced lymphocytes of the present invention may be prepared in the form of a cell preparation. The cell preparation of the present invention contains the CAR polynucleotide-introduced lymphocytes of the present invention in a therapeutically effective amount. For example, $1\times10^4$ to $1\times10^{10}$ cells are contained for one administration (one dose). The cell preparation may contain dimethylsulfoxide (DMSO) or serum albumin for the purpose of cell protection, antibiotics for the purpose of preventing bacterial contamination, and various components for (for example, vitamins, cytokine, growth factors, and steroids) for the purpose of cell activation, proliferation, or inductive differentiation.

The administration route of the CAR polynucleotide-introduced lymphocytes or cell preparation of the present invention is not particularly limited. For example, they are administered by intravenous injection, intraarterial injection, intraportal injection, intradermal injection, hypodermic injection, intramuscular injection, or intraperitoneal injection. Local administration may be used in place of systemic administration. Examples of the local administration include direct injection into the target tissues, body parts, and organs. The administration schedule may be made according to the sex, age, body weight, and pathology of the subject (patient). A single dose or continuous or periodical multiple doses may be used.

In the treatment method using the CAR polynucleotide-introduced lymphocytes of the present invention, a therapeutically effective amount of the CAR polynucleotide-introduced lymphocytes is administered to a patient. The CAR polynucleotide-introduced lymphocytes of the present invention exhibit the characteristic of exerting an antitumor effect on tumors that express EPHB4 protein on the cell membrane surface by their characteristic construction. Therefore, they can be used to treat specific tumor groups, i.e., soft tissue tumor (such as rhabdomyosarcoma), bone tumor, brain tumor (such as glioblastoma), lung cancer, bowel cancer, malignant mesothelioma, esophagus cancer, breast cancer, ovarian cancer, melanoma, and head and neck cancer.

4. Vector and Kit for Preparing CAR Polynucleotide-Introduced Lymphocytes

Another aspect of the present invention relate to a vector (CAR polynucleotide-introduced lymphocyte preparation vector) and a kit (CAR polynucleotide-introduced lymphocyte preparation kit) usable in the preparation method of the present invention. The CAR polynucleotide-introduced lymphocyte preparation vector of the present invention includes a CAR expression cassette, and allows the introduction of the expression cassettes into the target cell. The CAR expression cassette includes the CAR polynucleotide, a promoter necessary for the expression of the CAR polynucleotide (for example, CMV-IE, SV40ori, retrovirus LTP, SRα, EF1α, or β actin promoter). The vector of the present invention may include a polynucleotide for detection (for example, reporter gene, cell or tissue-specific gene, or selectable marker gene), an enhancer sequence, and a WRPE sequence.

Preferably, the vector of the present invention is constructed as a vector used in the transposon method. In this case, typically, the vector has a structure wherein a CAR expression cassette is sandwiched between a pair of transposon inverted repeat sequences (for example, they are disposed in this order: 5' end transposon inverted repeat sequence, CAR expression cassette, and 3' end transposon inverted repeat sequence).

One embodiment of the kit of the present invention is suitable to the method for preparing CAR polynucleotide-introduced lymphocytes using the transposon method. The kit contains the CAR vector including the CAR expression cassette sandwiched between a pair of transposon inverted repeat sequences, and a transposase expression vector. The transposase is selected so as to correspond to the pair of transposon inverted repeat sequences integrated into the CAR vector. For example, a combination of a piggyBac inverted repeat sequence and piggyBac transposase is used.

The kit of the present invention may include the reagent, instrument, or apparatus used for the gene introduction operation, and the reagent, instrument, or apparatus used for the detection and selection of the transformant. An instruction manual is usually attached to the kit of the present invention.

EXAMPLES

The following study was made to further advance the clinical application of CAR therapy.

<Cytocidal Effect of EPHB4-CAR-T Cells>

1. Material and Method (1) Preparation of pIRII-EPHB4-CAR Vector (I) The previously-reported CD19.CAR expression piggyBac transposon vector (pIRII-CAR.CD19) (Saito S, Nakazawa Y, Sueki A, Matsuda K, Tanaka M, Yanagisawa R, Maeda Y, Sato Y, Okabe S, Inukai T, Sugita K, Wilson M H, Rooney C M, Koike K. Anti-leukemic potency of piggyBac-mediated CD19-specific T cells against refractory Philadelphia chromosome-positive acute lymphoblastic leukemia. Cytotherapy. 2014; 16; 1257-69) was cleaved with both restriction enzymes XhoI and BbvCI (New England Biolab, Ipswich, MA, USA).

(II) mRNA was extracted from human neuroblastoma cell line SH-SY5Y, which is known to highly express EFNB2 genes, and cDNA was synthesized. EFNB2 is a membrane-bound protein having a sequence of 333 amino acids (SEQ ID NO: 2), and its extracellular domain (SEQ ID NO: 1) is known to include amino acids up to the 227th amino acid from the N-terminus. A PCR primer capable of specifically amplifying this site (XhoI-EFNB2 forward primer: ATCTCGAGATGGCTGTGAGAAGGG (SEQ ID NO: 9) and an EFNB2 ECD-BbvCI reverse primer: ATCCTCAG-CATAAGGCCACTTCGGAAC (SEQ ID NO: 10)) was prepared, and the previously obtained cDNA was used as a template to perform a PCR reaction. In this PCR primer sequence, an XhoI restriction enzyme recognition site was inserted in the Forward primer, and a BbvCI recognition site was inserted in the Reverse primer, in advance.

(III) The 699 bp DNA fragment obtained in (II) was cloned into a pCR-Blunt plasmid using ZeroBlunt PCR Cloning Kit (Thermo Fisher Scientific, Carlsbad, CA, USA). Using this plasmid, E. coli was transformed, mass-amplified, and extracted. The pCR-Blunt plasmid into which the extracted EFNB2 extracellular domain base sequence was inserted was cleaved with both restriction enzymes XhoI and BbvCI.

(IV) The 4971 bp DNA fragment obtained in (I) and the 689 bp DNA fragment obtained in (III) were ligated using DNA Ligation kit (Takarabio, Otsu, Shiga, Japan).

(V) Competent cells were used to mass-amplify the 5660 bp circular DNA plasmid (SEQ ID NO: 4) obtained in (IV).

(VI) The entire base sequence was confirmed using Applied Biosystems 3130 Genetic Analyzer (Applied Biosystems, Waltham, MA, USA) (see the Sequence Listing).

(2) Preparation of EPHB4-CAR-T Cells (I) Mononuclear cells (PBMC) were separated from about 10 ml of peripheral blood using specific gravity centrifugation.

(II) The pIRII-EPHB4-CAR vector (5 µg) and the pCMV piggyBac vector (5 µg) were gene-introduced into $1 \times 10^7$ PBMCs using electroporation (Program EO-115) by combination of 4D-Nucleofector™ device and P3 Primary Cell 4D-Nucleofector™X kit (Lonza, Basel, Switzerland).

(III) $1 \times 10^6$ irradiated PBMCs pulsed with four viral antigen peptides (MACS GMP PepTivator®; AdV5 Hexon, CMV pp65, EBV EBNA-1, EBV BZLF1, Miltenyi Biotec, Auburn, CA) were mixed with the gene-introduced cells obtained in (II). The mixtures were placed in one well of a 24-well culture plate which was filled with 2 ml of Tex-MACS™ medium (Miltenyi) added with interleukin (IL)-7 (10 ng/ml, Miltenyi) and IL-15 (5 ng/ml, Miltenyi) and also which was immobilized with an anti-CD28 antibody (Miltenyi). Three days after gene introduction, gene-introduced cells were transferred to one well of a non-immobilized 24-well culture plate. At that time, 1 ml of the IL-7/IL-15-added TexMACS™ medium was exchanged. Seven days after gene introduction, the gene-introduced cells were transferred to a G-Rex 10 incubator (Wilson Wolf Manufacturing Inc, New Brighton, MN) filled with 30 ml of a TexMACS™ medium added with IL-7/IL-15 (5 ng/ml). The cells were recovered on Day 14 after gene introduction. The expression of CAR protein was confirmed by flow cytometry using part of the cells. The thus-prepared CAR-T cells are referred to as EPHB4-CAR-T cells. As a control group, CD19-CAR-T cells in which the previously reported pIRII-CAR.CD19 vector was gene-introduced were also amplified and cultured in the same manner.

(3) Co-Culture Experiment 1

As a highly EPHB4-expressing tumor, a tumor cell line Rh30 (in which EPHB4 was highly expressed and CD19 was low expressed) of rhabdomyosarcoma which is one of the typical childhood cancers was used. Human B cell lymphoma Raji cells (in which EPHB4 was low expressed and CD19 was highly expressed) were used as a control low EPHB4-expressing tumor. Into one well of a 24-well culture plate, $2 \times 10^5$ CAR-T cells (CD19-CAR-T cells or EPHB4-CAR-T cells) and $1 \times 10^5$ tumor cells (Rh30 cells or Raji cells) were inserted (a ratio of CAR-T cells to tumor cells: 2:1), and co-cultured in 1 ml of a 10% fetal bovine serum-containing DMEM medium for 3 days. Three wells were prepared for each combination.

At 0 hours and 72 hours after the start of co-culture, cells were recovered for each well, and stained with an anti-CD3-APC antibody and an anti-IGF1R-PE antibody. Then, the ratio of CD3-positive cells (T cells) to IGF1R-positive cells (Rh30 cells) was measured by flow cytometry. The control Raji cells were stained with the anti-CD3-APC antibody and the anti-CD19-FITC antibody, and then the ratio of CD3-positive cells (T cells) to CD19-positive cells (Raji cells) was measured by flow cytometry.

(4) Co-Culture Experiment 2

CD19-CAR-T cells or EPHB4-CAR-T cells and Rh30 cells were co-cultured in a cell ratio of 2:1, and ELISA was performed to quantify IFNγ released into the culture supernatant on Day 0 and Day 3 of co-culture.

2. Results

The construction of the EPHB4-CAR expression vector (pIRII-EPHB4-CAR) in which the EFNB2 extracellular domain was inserted as the antigen recognition site is shown in FIG. 1. In addition, the nucleotide sequence (SEQ ID NO: 4) of the EPHB4-CAR expression vector is shown in the Sequence Listing. The sequence of SEQ ID NO: 4 includes a region (6 bp to 687 bp, SEQ ID NO: 5) encoding the EphrinB2 extracellular domain, a linker sequence (SEQ ID NO: 6), a region (702 bp to 1022 bp, SEQ ID NO: 7) encoding CD28 (including the transmembrane domain and the intracellular domain), and a region encoding the CD35 intracellular domain chain (1023 bp to 1361 bp, SEQ ID NO: 8).

Figure 2:
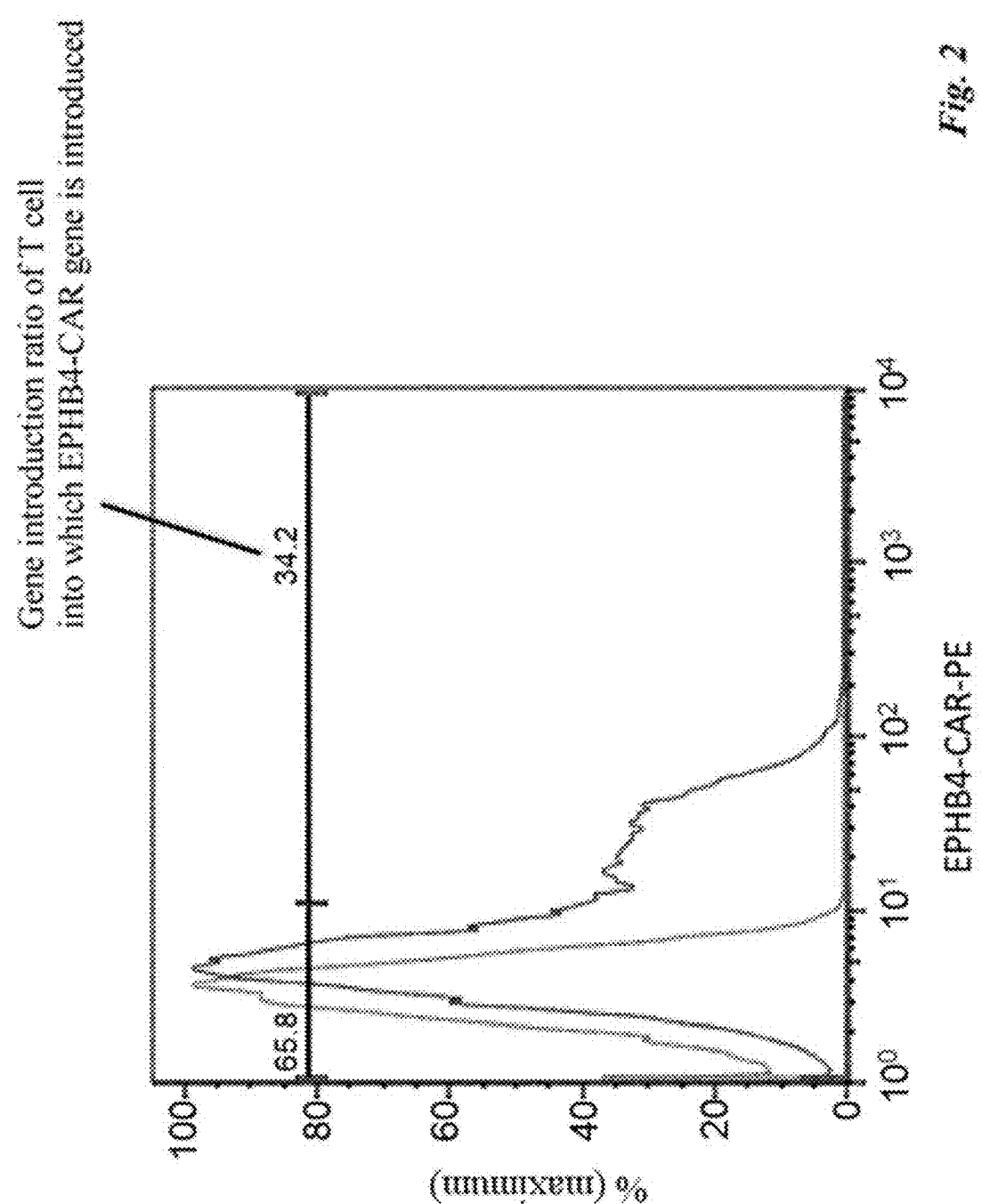
FIG. 2 shows the expression rate of EPHB4-CAR on T cells. The CAR gene introduction rate of T cells on Day 15 after gene introduction operation using an EPHB4-CAR expression vector and a pCMV-piggyBac vector was measured by flow cytometry.

As a result of examining the CAR expression rate on the T cells on Day 15 after gene introduction, it was 34.2% (FIG. 2) for the T cells into which the EPHB4-CAR polynucleotide was introduced, and 55.1% for the T cells into which the CD19-CAR polynucleotide was introduced.

Figure 3A:
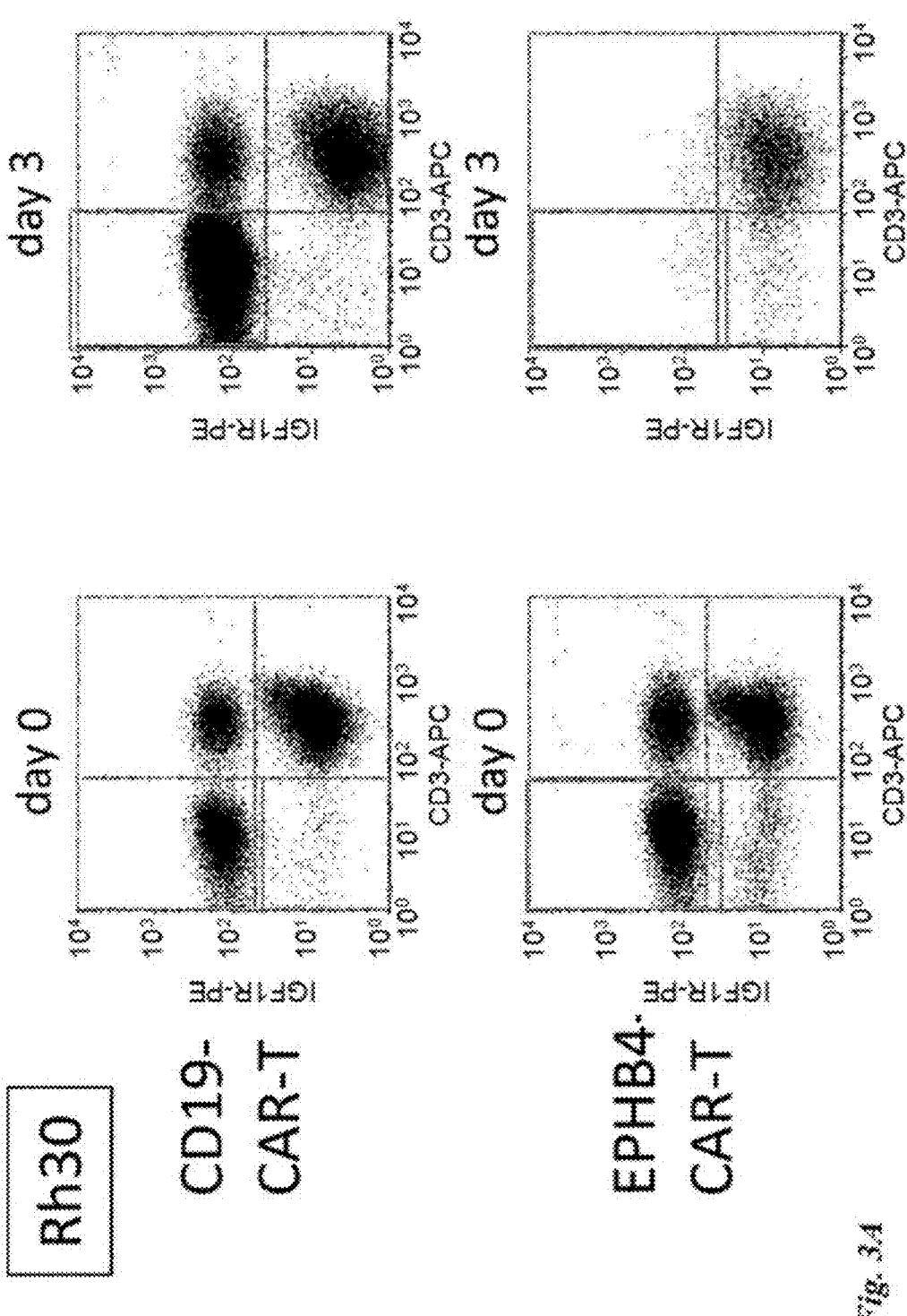
FIG. 3A shows results of flow cytometry analysis of tumor cells (Rh30 cells) co-cultured with CAR-T cells (CD19-CAR-T cells or EPHB4-CAR-T cells) on Day 0 and Day 3. CAR-T cells (CD19-CAR-T cells or EPHB4-CAR-T cells) and tumor cells (Rh30 cells or Raji cells) were co-cultured in a cell ratio of 2:1
Figure 3B:
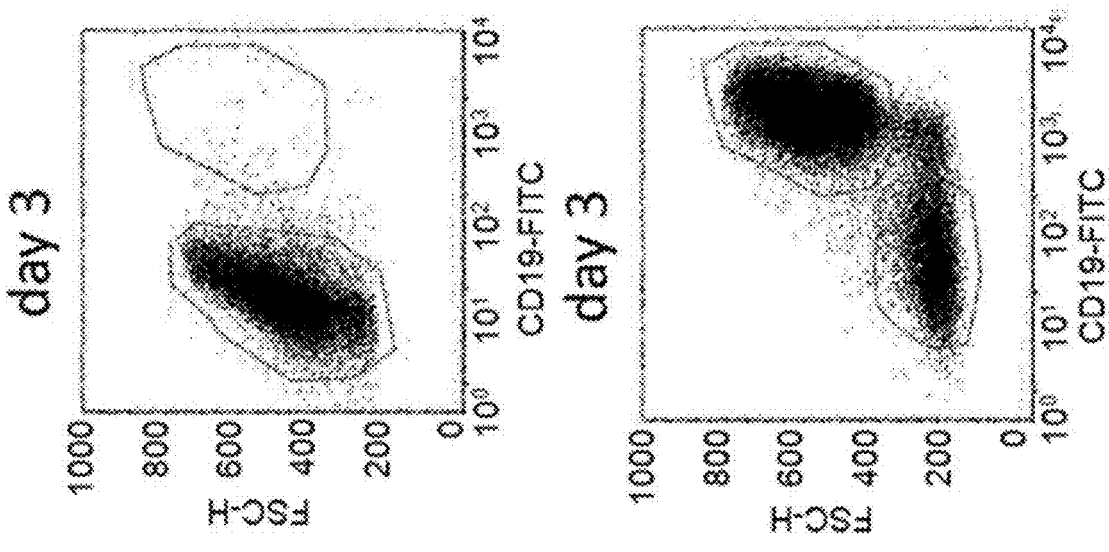
FIG. 3B shows results of flow cytometry analysis of tumor cells (Rh30 cells) co-cultured with CAR-T cells (CD19-CAR-T cells or EPHB4-CAR-T cells) on Day 0 and Day 3. CAR-T cells (CD19-CAR-T cells or EPHB4-CAR-T cells) and tumor cells (Rh30 cells or Raji cells) were co-cultured in a cell ratio of 2:1
Figure 3B:
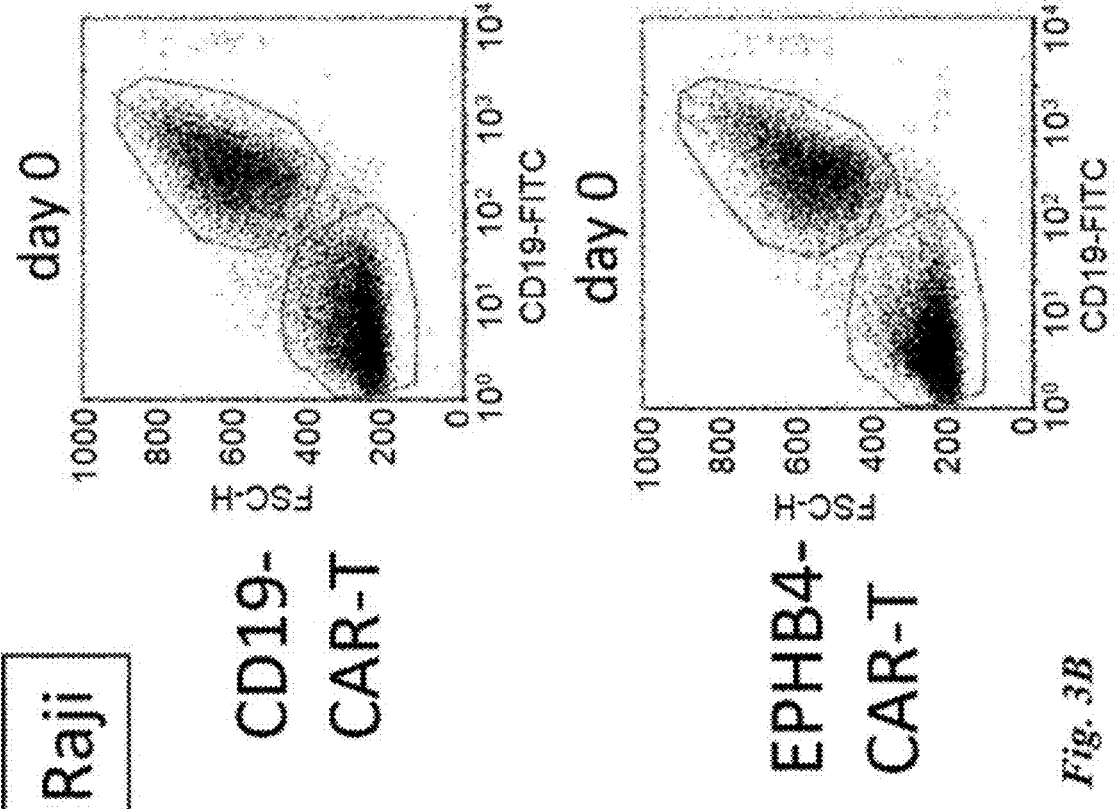
Figure 3C:
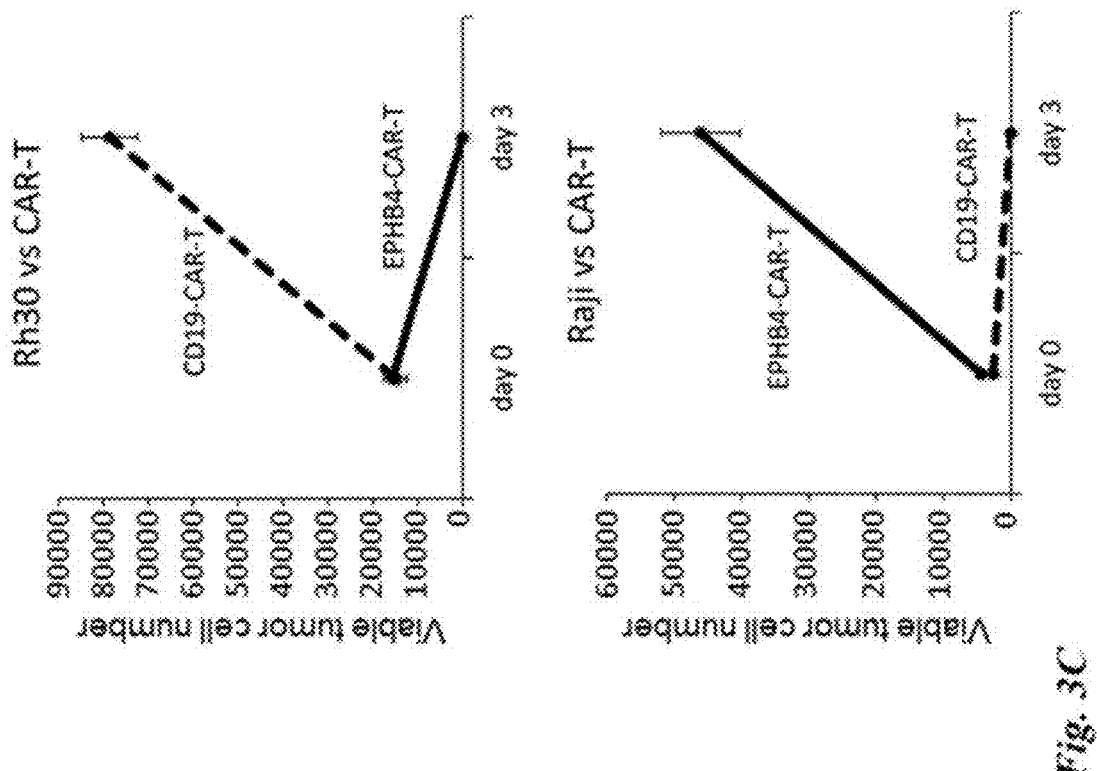
FIG. 3C shows tumor cell proliferation inhibitory effect by EPHB4-CAR-T cells. CAR-T cells (CD19-CAR-T cells or EPHB4-CAR-T cells) and tumor cells (Rh30 cells or Raji cells) were co-cultured in a cell ratio of 2:1. On Day 0 and Day 3 of co-culture, the number of surviving tumor cells was measured by flow cytometry. The same experiment was repeated three times to calculate an average value. Upper: Proliferation inhibitory effect on Rh30 cells. Lower: Proliferation inhibitory effect on Raji cells.

The results of co-culture experiment 1 are shown in FIG. 3A, FIG. 3B and FIG. 3C and the following table. The EPHB4-CAR-T cells exhibited a high proliferation inhibitory effect specifically for the tumor (Rh30) in which EPHB4 was highly expressed.

TABLE 1

| | Rh30 (Rhabdomyosarcoma cell) | | Raji (B-cell lymphoma cells) | |
|---|---|---|---|---|
| | Day 0 | Day 3 | Day 0 | Day 3 |
| EPHB4-CAR-T cell | 15622 ± 1745 | 77 ± 14 | 4440 ± 259 | 46064 ± 5862 |
| CD19-CAR-T cell | 14796 ± 576 | 78571 ± 6279 | 2633 ± 224 | 41 ± 9 |

Figure 4:
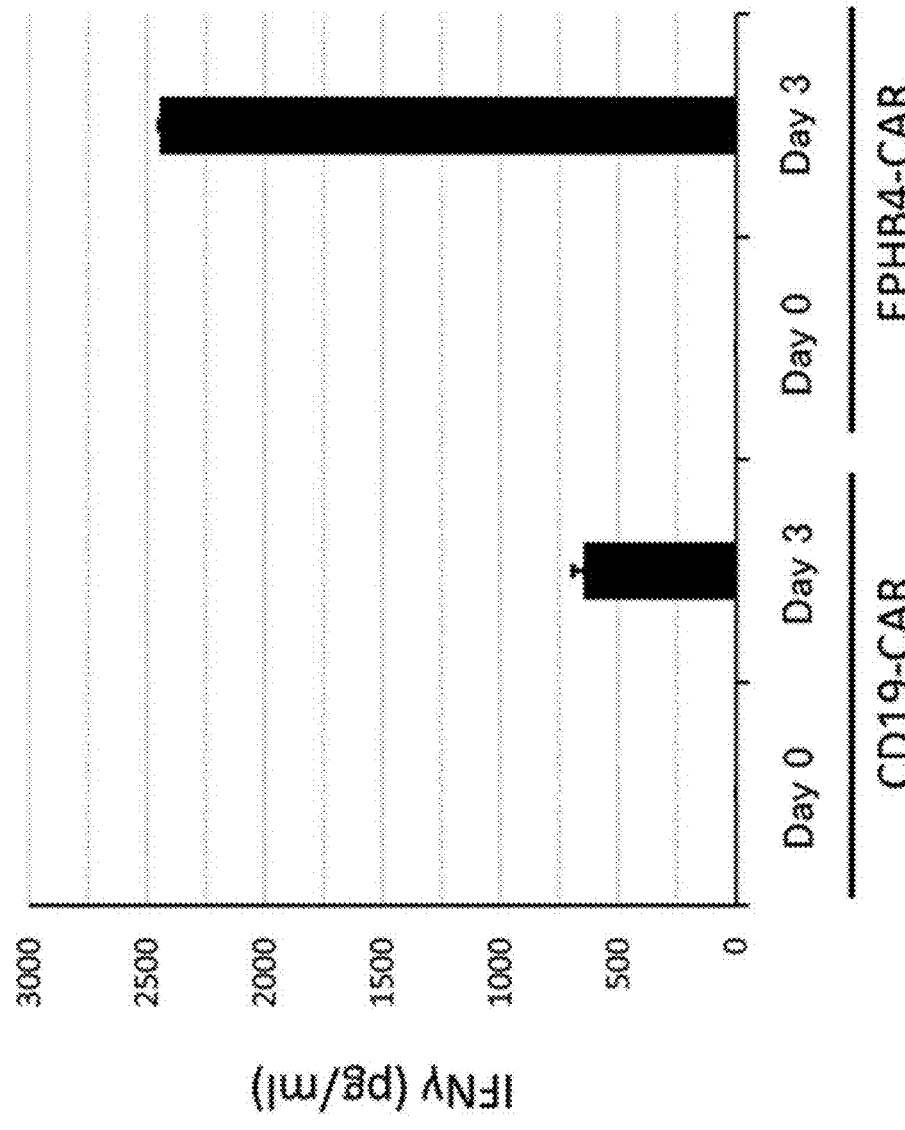
FIG. 4 shows IFNγ production ability of EPHB4-CAR-T cells. CAR-T cells (CD19-CAR-T cells or EPHB4-CAR-T cells) and Rh30 cells were co-cultured in a cell ratio of 2:1. IFNγ released into the culture supernatant was quantified by the ELISA method on Day 0 and Day 3 of co-culture. The same experiment was repeated three times to calculate an average value.

The results of co-culture experiment 2 are shown in FIG. 4. As corresponding to the results of co-culture experiment 1, the EPHB4-CAR-T cells were activated on Day 3 of co-culture and highly produced IFNγ.

3. Discussion

The EPHB4-CAR-T cells selectively and potently induced cell death to rhabdomyosarcoma cells in which EPHB4 was highly expressed. That is, it has been proved that the EPHB4-CAR-T cell developed this time can specifically kill a tumor in which EPHB4 is highly expressed. Therefore, treatment with the EPHB4-CAR-T cells (CAR-T therapy) is promising as a novel method for treating rhabdomyosarcoma. The EPHB4-CAR-T cells are greatly expected to be applied to the treatment of various tumors/cancers in which EPHB4 is highly expressed, such as rhabdomyosarcoma, lung cancer, bowel cancer, malignant mesothelioma, esophagus cancer, breast cancer, ovarian cancer, melanoma, and head and neck cancer.

<Animal Experiment>

The cytocidal effect of the EPHB4-CAR-T cells was verified in a mouse model. Tumor-carrying mice were prepared by subcutaneously inoculating immunodeficient mice (SCID Beige mice) with $2 \times 10^6$ rhabdomyosarcoma cell lines Rh30 labeled with firefly luciferase.

One week after inoculation, $10 \times 10^6$ CAR-T cells (CD19-CAR-T cells or EPHB4-CAR-T cells) were intravenously injected from the tail vein. The tumor size was then assessed every 7 days using the IVIS live imaging system (Sumisho Pharma International Co., Ltd.).

Figure 5:
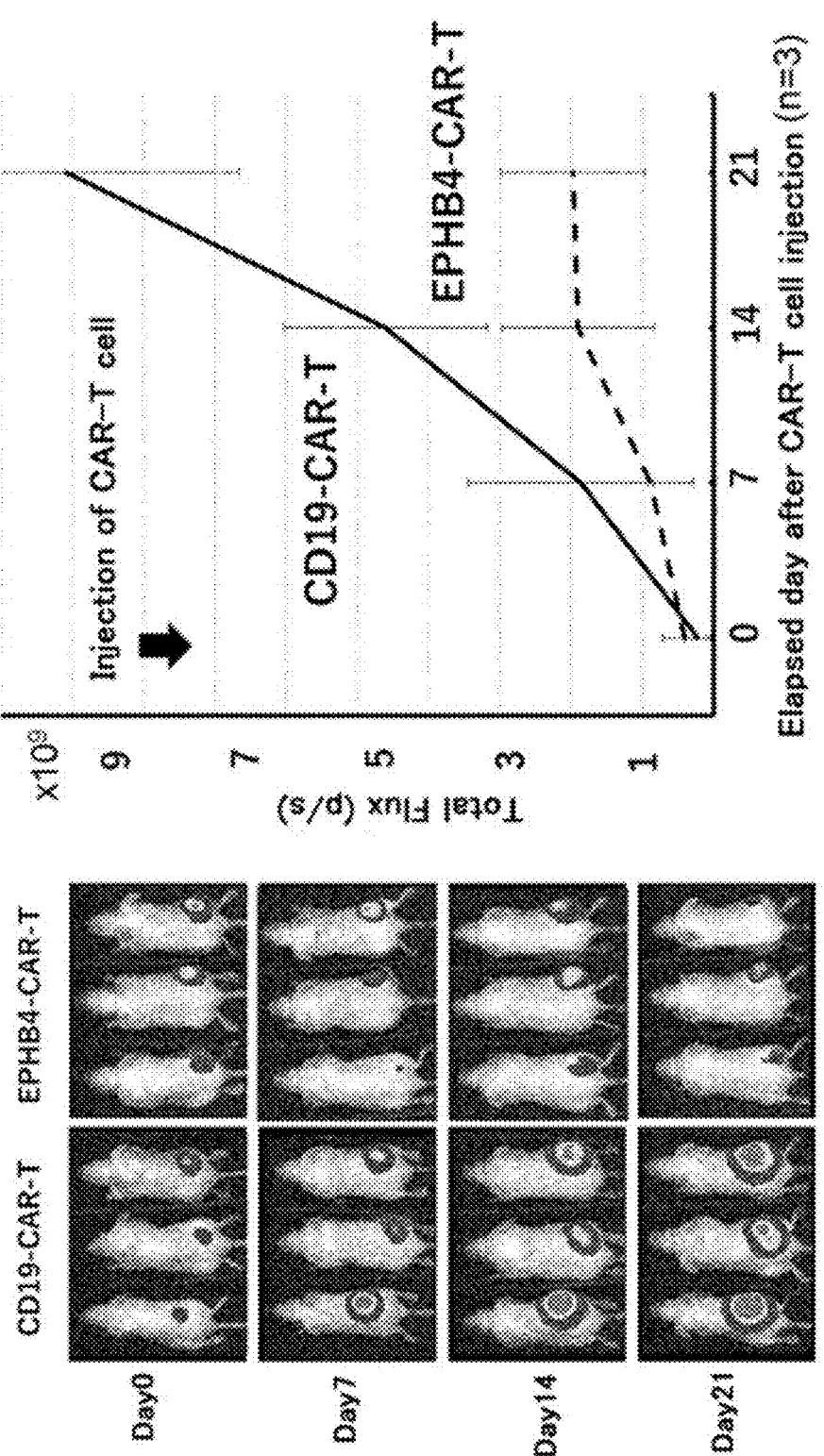
FIG. 5 shows the results of an experiment (live imaging) using mouse models. The tumor size was assessed every 7 days (right) by live imaging (left) after injection of CAR-T cells into tumor-bearing mice.

As shown in FIG. 5, a marked increase in the tumor was observed in the CD19-CAR-T cell administration group, while the EPHB4-CAR-T administration group showed a tumor growth suppressive effect.

<Cytocidal Effect of EPHB4-CAR-T Cells Against EPHA2-Positive and EPHB4-Negative Tumor Cells>

In order to demonstrate the unexpected effect such that EPHB4-CAR-T cells are effective in suppressing not only the proliferation of EphA2 negative-EphB4 positive tumor cells, but also the proliferation of EphA2 positive-EphB4 negative tumor cells, the experiment below was carried out.

1. Method i. Flow Cytometry

Cell-surface expression of EPHA2 and EPHB4 on neuroblastoma cell lines SK-N-AS (EPHA2-positive and EPHB4-negative) and SY-SY5Y (EPHA2-negative and EPHB4-positive), respectively, was determined by flow cytometry using phycoerythrin (PE)-conjugated EPHA2 antibodies (BioLegend) and EPHB4 (R&D SYSTEMS). All flow cytometry data were acquired using a BD Accuri C6 Plus (BD Biosciences) and analyzed using FlowJo® Software (BD Biosciences, flow cytometry analysis software).

ii. Cytotoxicity Assay

SK-N-AS (EPHA2-positive) and SH-SY5Y (EPHB4-positive) neuroblastoma cell lines were plated on xCELLigence® E-plates 16 (real-time cell analysis, RTCA) (ACEA Biosciences, San Diego, CA, USA) at a density of $0.5$-$10^4$/well 18-24 h prior to CAR-T cell seeding. EPHB4-targeted CAR-T cells were added at an effector cells: tumor cells ratio of 1:2, 1:1, or 2:1; then, real-time impedance was measured for 120 h and presented as the normalized cell index using an xCELLigence® RTCA DP system. Data were analyzed using Software v2.0 (ACEA Biosciences).

2. Results

As shown in FIG. 6 below, A-1 and A-2 reflect that the T cells expressing EPHB4-targeted CAR recited in claim 1 suppress proliferation of EPHA2 positive-EPHB4 negative tumor cells. B-1 and B-2 in FIG. 1 reflect that the T-cells recited in claim 1 also suppress proliferation of EPHA2 negative-EPHB4 positive tumor cells.

Figure 6A:
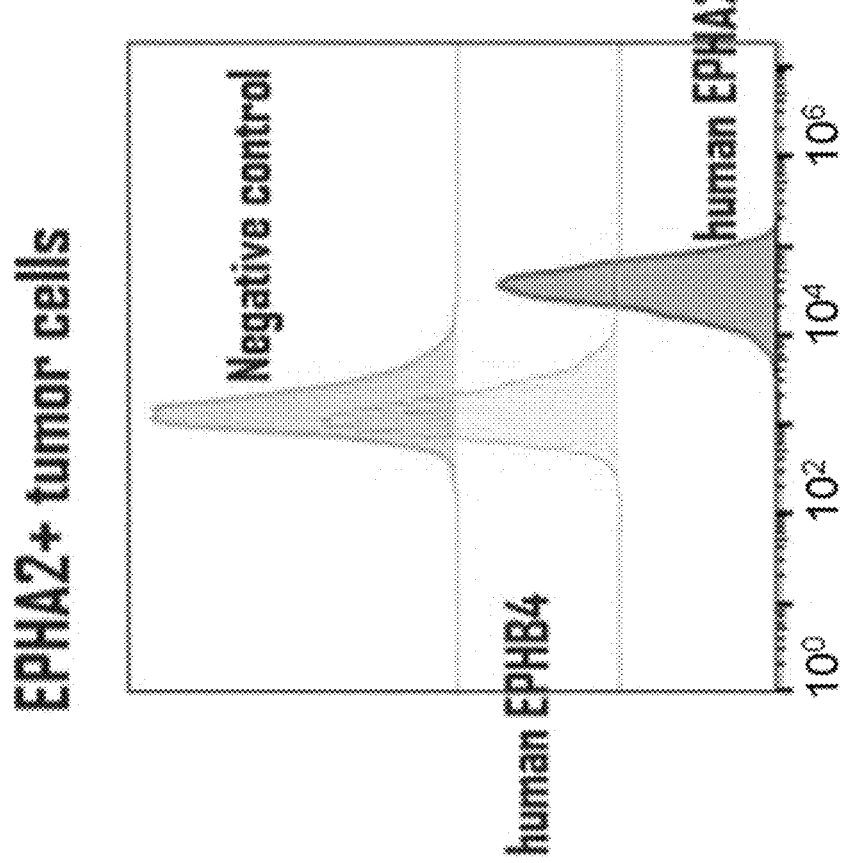
FIG. 6A shows the results of antigen analysis by flow cytometry on SK-N-AS (EPHA2-positive and EPHB4-negative) cells.
Figure 6B:
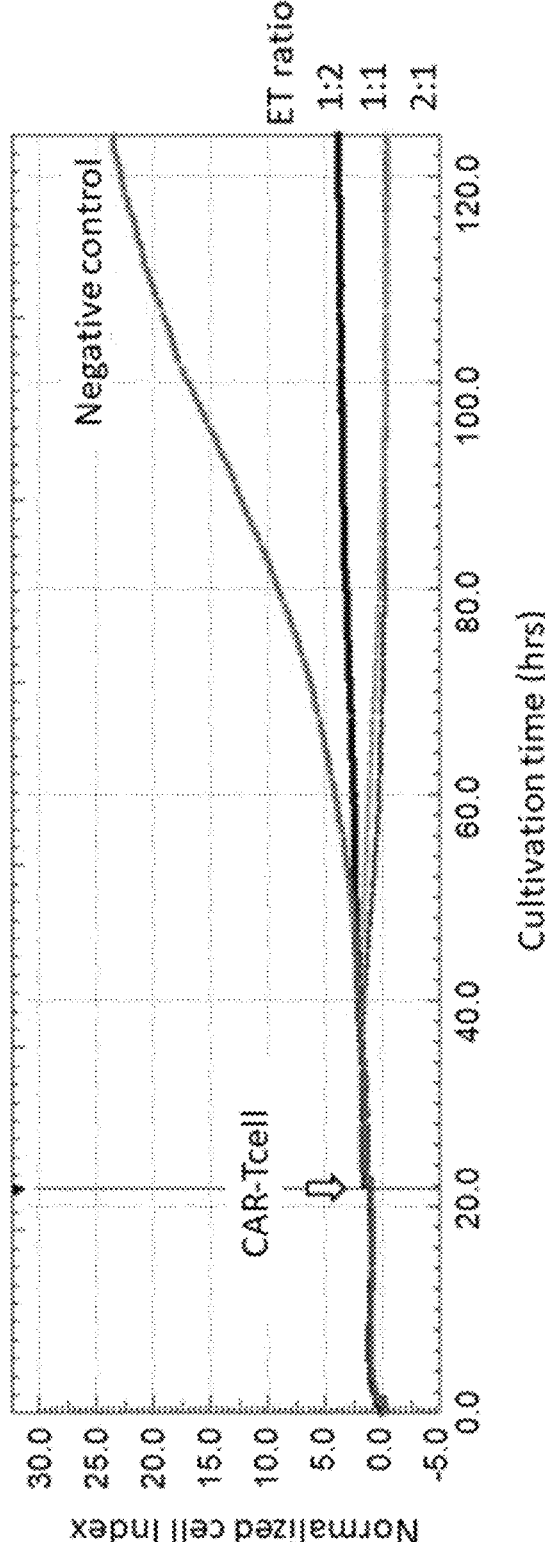
FIG. 6B shows the results of a cell proliferation curve of negative control (only SK-N-AS cells), EPHB4-targeted CAR-T cells with SK-N-AS cells in a ratio of 1:2, 1:1, or 2:1. The symbol "E" indicates EPHB4-tageted CAR-T cells and the symbol "T" indicates tumor cells.
Figure 7A:
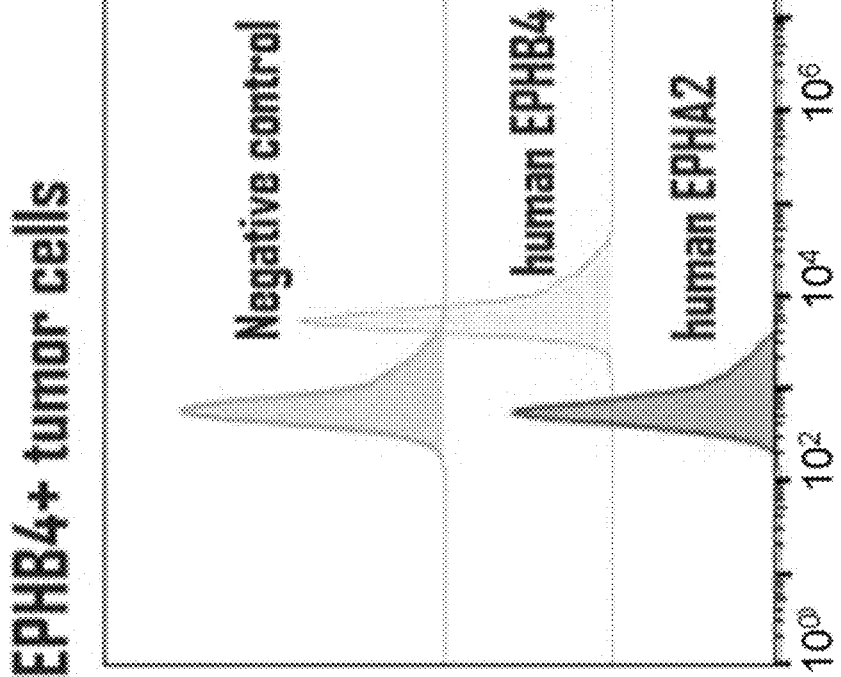
FIG. 7A shows the results of antigen analysis by flow cytometry on SY-SY5Y (EPHA2-negative and EPHB4-positive) cells.
Figure 7B:
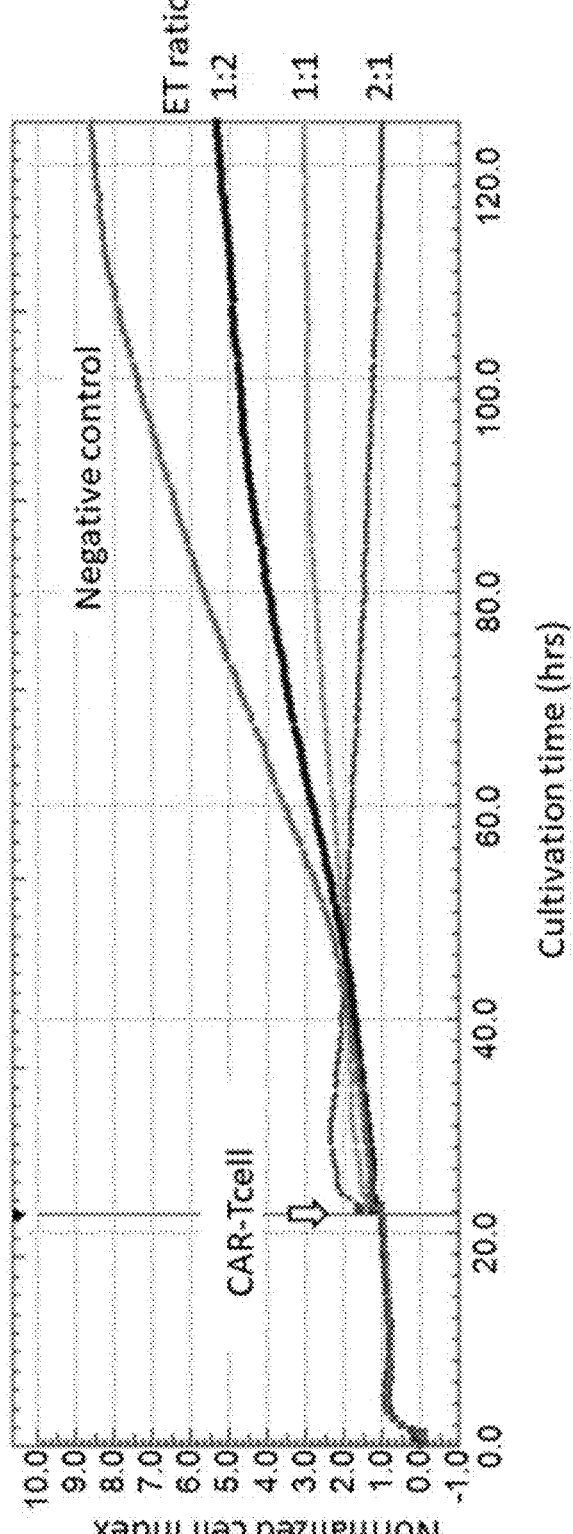
FIG. 7B shows the results of a cell proliferation curve of negative control (only SY-SY5Y cells), EPHB4-targeted CAR-T cells with SY-SY5Y cells in a ratio of 1:2, 1:1, or 2:1. The symbol "E" indicates EPHB4-targetd CAR-T cells and the symbol "T" indicates tumor cells.

FIG. 6A shows the results of antigen analysis by flow cytometry on SK-N-AS (EPHA2-positive and EPHB4-negative) cells. When the anti-EPHA2 antibody is used, the peak of the cell number shifts to the right. These results indicate that SK-N-AS cells are EPHA2-positive and EPHB4-negative tumor cells. FIG. 6B shows the results of a cell proliferation curve of negative control (only SK-N-AS cells), EPHB4-targeted CAR-T cells with SK-N-AS cells in a ratio of 1:2, 1:1, or 2:1. When SK-N-AS cells were co-cultured with EPHB4-targeted CAR-T cells, the tumor cell number decreased in comparison with only SK-N-AS cells. FIG. 7A shows the results of antigen analysis by flow cytometry on SY-SY5Y (EPHA2-negative and EPHB4-positive) cells. When the anti-EPHB4 antibody is used, the peak of the cell number shifts to the right. These results indicate that SY-SY5Y cells are EPHA2-negative and EPHB4-positive tumor cells. FIG. 7B shows the results of a cell proliferation curve of negative control (only SY-SY5Y cells), EPHB4-targeted CAR-T cells with SY-SY5Y cells in a ratio of 1:2, 1:1, or 2:1. When SY-SY5Y cells were co-cultured with EPHB4-targeted CAR-T cells, the tumor cell number decreased in comparison with only SY-SY5Y cells.

The normalized cell index (vertical axis) increases in accordance with an increase in the cell number.

INDUSTRIAL APPLICABILITY

Cell therapy (CAR therapy) using gene-modified lymphocytes (T cells, NK cells, etc.) into which a chimeric antigen receptor (CAR) polynucleotide or a T cell receptor (TCR) gene is introduced is expected as an effective treatment method for refractory cancer. The CAR polynucleotide-introduced lymphocytes provided by the present invention are specific to EPHB4 or EPHA2-expressing cells and are, for example, promising therapeutic agents (cell preparations) for rhabdomyosarcoma. That is, the CAR polynucleotide-introduced lymphocytes of the present invention can be expected to induce cell death selectively and potently to rhabdomyosarcoma cells in which EPHB4 or EPHA2 is expressed. Rhabdomyosarcoma is a typical refractory childhood cancer, and the prognosis for advanced rhabdomyosarcoma is extremely poor, and the development of new treatment is highly desired. The present invention meets such needs, and the significance thereof is extremely large.

The present invention is not limited to the description of the embodiments and examples of the present invention at all. Various modifications that can be easily achieved by those skilled in the art without departing from the claims also fall within the scope of the invention. The contents of the articles, the patent laid-open publications, patent publications, and the like specified herein shall be cited by incorporation in their entity.

SEQUENCE LISTING FREE TEXT

SEQ ID NO: 3: Explanation of artificial sequences: EFNB2-CAR polynucleotide

SEQ ID NO: 4: Explanation of artificial sequences: pIRII-EFNB2-CAR vector

SEQ ID NO: 6: Explanation of artificial sequence: linker

SEQ ID NO: 9: Explanation of artificial sequences: XhoI-EFNB2 forward primer

SEQ ID NO: 10: Explanation of artificial sequences: EFNB2 ECD-BbvCI reverse primer

---

The invention claimed is:

1. A chimeric antigen receptor comprising an extracellular domain including an EphrinB2 extracellular domain, a transmembrane domain, and an intracellular signal domain for the effector function of immunocytes, wherein the chimeric antigen receptor is encoded by the polynucleotide of SEQ ID NO: 3, and the EphrinB2 extracellular domain of the chimeric antigen receptor binds to Ephrin type-A receptor 2 (EPHA2) and Ephrin type-B receptor 4 (EPHB4).

2. An isolated gene-modified lymphocyte expressing the chimeric antigen receptor according to claim 1.

3. A treatment method comprising:
administering a therapeutically effective amount of the isolated gene-modified lymphocyte according to claim 2 to a patient,
wherein the patient has a tumor expressing EPHA2 or a cancer expressing EPHA2, or the patient has a tumor expressing EPHB4 or a cancer expressing EPHB4.

* * * * *